United States Patent [19]

Jones et al.

[11] Patent Number: 4,795,755
[45] Date of Patent: Jan. 3, 1989

[54] HETEROCYCLIC DERIVATIVES

[75] Inventors: Derrick F. Jones, Macclesfield; Keith Oldham, Cheadle, both of England

[73] Assignee: Imperial Chemical Industries PLC, London, Great Britain

[21] Appl. No.: 353,384

[22] Filed: Mar. 1, 1982

[30] Foreign Application Priority Data

Mar. 18, 1981 [GB] United Kingdom ............... 8108407
Oct. 29, 1981 [GB] United Kingdom ............... 8132680

[51] Int. Cl.$^4$ ............... A61K 31/495; C07D 403/04
[52] U.S. Cl. ............... 514/383; 544/218;
544/295; 544/296; 544/298; 544/331; 544/333;
544/357; 544/364; 544/366; 544/367; 544/369;
548/128; 548/130; 548/131; 548/133; 548/184;
548/190; 548/191; 548/194; 548/225; 548/228;
548/235; 548/252; 548/255; 548/263; 548/265;
548/266; 548/267; 548/269; 548/336; 548/348;
548/374
[58] Field of Search ............... 548/269, 128, 130, 131,
548/133, 184, 190, 191, 194, 225, 228, 235, 252,
255, 263, 265, 266, 267, 336, 348, 374; 424/269;
514/359, 361, 364, 369, 370, 376, 377, 383, 384,
397, 402, 406–407

[56] References Cited

U.S. PATENT DOCUMENTS

| | | |
|---|---|---|
| 4,165,377 | 8/1979 | Jones et al. |
| 4,165,378 | 8/1979 | Gilman et al. |
| 4,242,350 | 12/1980 | Yellin et al. |
| 4,242,351 | 12/1980 | Yellin et al. |
| 4,252,819 | 2/1981 | Hirata |
| 4,315,009 | 2/1982 | Jones et al. |
| 4,342,765 | 8/1982 | Jones et al. |
| 4,362,728 | 12/1982 | Yellin et al. |

FOREIGN PATENT DOCUMENTS

| | | |
|---|---|---|
| 866155 | 4/1977 | Belgium . |
| 0035228 | 9/1981 | European Pat. Off. . |
| 35228 | 9/1981 | European Pat. Off. . |
| 0050407 | 4/1982 | European Pat. Off. . |
| 2003471 | 3/1979 | United Kingdom . |
| 2052478 | 1/1981 | United Kingdom . |
| 2055800 | 3/1981 | United Kingdom . |
| 2085871A | 5/1982 | United Kingdom . |

OTHER PUBLICATIONS

"Derwent Abstracts", 48522, D/27, B03, Yama 10/12/79, p. 87.
"Derwent Abstracts", 82525 D/45, B03, Yama 2/29/80, p. 33.
"Derwent Abstracts", 22898 E/12, B03(B02), Yama 7/22/80, p. 76.
"Derwent Abstracts", 22901 E/12, B03, Yama 7/22/80, p. 78.
"Derwent Abstracts", 22902 E/12, B03, Yama 7/23/80, p. 79.
"Derwent Abstracts", 74415 C/42, B03, Yama 2/28/79.
"Derwent Abstracts", 74408 C/42, B03, Yama, 3/2/79.

*Primary Examiner*—Glennon H. Hollrah
*Assistant Examiner*—James H. Turnipseed
*Attorney, Agent, or Firm*—Cushman, Darby & Cushman

[57] ABSTRACT

This invention relates to heterocyclic derivatives which are histamine H-2 antagonists and which inhibit gastric acid secretion. According to the invention there is provided a guanidine derivative of the formula I:

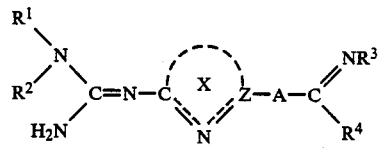

in which $R^1$ and $R^2$, same or different, are hydrogen or 1–10C alkyl, 3–8C cycloalkyl, 4–14C cycloalkylalkyl, each alkyl, cycloalkyl or cycloalkylalkyl optionally carrying one or more F, Cl or Br atoms, provided that one of $R^1$ and $R^2$ is halogen-substituted, or $R^2$ is hydrogen and $R^1$ is $R^5$-E-W- in which W is 2–6 alkylene optionally substituted by 1 or 2 1–4C alkyls, E is O,S,-SO,SO$_2$ or NR$^6$ in which R$^6$ is H or 1–6C alkyl, $R^5$ is H or 1–6C alkyl optionally substituted by 1 or 2 1–4C alkyls, or $R^5$ and $R^6$ are joined to form a pyrrolidine, piperidine, morpholine, piperazine or N-methylpiperazine ring; ring X is a heterocyclic ring as defined in the specification; A is phenylene or 5–7C cycloalkylene, or a 1–8C alkylene into which is optionally inserted one or two groups; and $R^3$ and $R^4$ are a variety of radicals described in the specification: and the pharmaceutically-acceptable acid-addition salts thereof. Manufacturing processes and pharmaceutical compositions are also described.

10 Claims, No Drawings

HETEROCYCLIC DERIVATIVES

This invention relates to heterocyclic derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, Brit. J. Pharmac. 1966, 27, 427) and the action of histamine at this receptor is blocked (antagonised) by classical "antihistamine" drugs such as mepyramine. The second histamine receptor has been named the H-2 receptor (Black et al., Nature, 1972, 236, 385) and the action of histamine at this receptor is blocked by drugs such as cimetidine. It is known that one of the results of the blockade of this action of histamine at the H-2 receptor is the inhibition of the secretion of gastric acid and a compound which possesses this ability is therefore useful in the treatment of peptic ulcers and other conditions caused or exacerbated by gastric acidity.

In UK Patent Applications Nos. GB2052478A and GB2055800A there are described histamine H-2 receptor antagonists which are 2-guanidinothiazole derivatives carrying a side chain in the 4-position to the end of which is attached a substituted amidine group. It has now been discovered that a haloalkylguanidinoheterocycle carrying a side chain to the end of which is attached an optionally substituted amidine group is a potent histamine H-2 receptor antagonist.

According to the invention there is provided a guanidine derivative of the formula I:

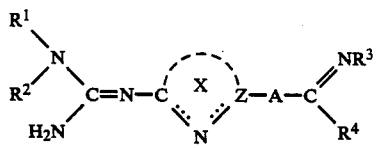

in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogensubstituted alkyl, cycloalkyl or cycloalkylalkyl radical and provided there is no halogen substituent on the carbon atom of the alkyl, cycloalkyl or cycloalkylalkyl radical which is directly attached to the nitrogen atom, or —$R^2$ is a hydrogen atom and —$R^1$ is a radical of the formula II:

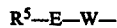

in which W is an unbranched 2–6C alkylene chain which is optionally substituted by one or two 1–4C alkyl radicals, E is an oxygen or sulphur atom, a sulphinyl or sulphonyl radical, or a radical of the formula $NR^6$ in which $R^6$ is a hydrogen atom or a 1–6C alkyl radical, $R^5$ is a hydrogen atom or an unbranched 1–6C alkyl radical which is optionally substituted by one or two 1–4C alkyl radicals, or $R^5$ and $R^6$ are joined to form, together with the nitrogen atom to which they are attached, a pyrrolidine, piperidine, morpholine, piperazine or N-methylpiperazine ring;

in ring X the dotted line is a double bond on one side of the nitrogen atom and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1–6C alkyl, 1–6C alkoxy, trifluoromethyl, hydroxy and amino radical.

A is a phenylene or a 5–7C cycloalkylene radical or a 1–8C alkylene chain which is optionally substituted by one or two 1–3C alkyl radicals and into which is optionally inserted, as part of the backbone of the chain, one or two groups selected from oxygen and sulphur atoms and NH, 1–6C N-alkyl, cis and trans vinylene, ethynylene, phenylene and 5–7C cycloalkylene radicals, provided that the shortest link between ring X and $C(R^4)=NR^3$ is of at least 3 atoms, provided that when an optional insertion is made in chain A which results in the inserted group being directly attached to $C(R^4)=NR^3$ the inserted group is other than an NH or N-alkyl radical, and provided that no two insertions selected from oxygen and sulphur atoms and NH and N-alkyl radicals are directly attached one to the other;

$R^3$ is a hydrogen atom or a 1–6C alkyl, 3–8C cycloalkyl, 4–14C cycloalkylalkyl, 1–6C haloalkyl, 1–6C hydroxyalkyl, 1–6C aminoalkyl, 2–10C alkylaminoalkyl, 3–14C dialkylaminoalkyl, 2–6C carboxyalkyl, 1–6C alkanoyl, 7–11C aroyl, 6–10C aryl, 7–11C arylalkyl, 2–6C alkenyl, 2–6C alkynyl, 2–6C haloalkanoyl, 1–6C thioalkanoyl, 7–11C thioaroyl, cyano, carbamoyl, thiocarbamoyl, 2–6C alkylcarbamoyl, 3–10C dialkylcarbamoyl, 2–6C alkylthiocarbamoyl, 3–10C dialkylthiocarbamoyl, carboxy, 2–6C alkoxycarbonyl, 2–6C alkoxythiocarbonyl, oxamoyl, sulphamoyl, 1–6C alkylsulphamoyl, 2–10C dialkylsulphamoyl, 6–10C arylsulphamoyl, 7–11C aralkylsulphamoyl, 1–6C alkanesulphonyl, 6–10C arenesulphonyl, hydroxy, 1–6C alkoxy, amino, 1–6C alkylamino, 2–10C dialkylamino, 6–10C arylamino, 2–6C alkoxycarbonylamino, 7–11C aryloxycarbonylamino, 1–6C alkanoylamino, 7–11C aroylamino, 1–6C thioalkanoylamino, 7–11C thioaroylamino, heteroarylcarbonylamino, heteroaryl-(1–6C)alkylcarbonylamino, 1–6C alkanesulphonylamino, 6–10C arenesulphonylamino, ureido, thioureido, oxamoylamino, heteroaryl or heteroaryl-(1–6C)alkyl radical;

$R^4$ is a radical of the formula $HNR^7$ in which $R^7$ is a hydrogen atom or a 1–6C alkyl, 2–6C alkenyl, 2–6C alkynyl, cyano, 1–6C alkanoyl, carbamoyl, 2–6C alkylcarbamoyl or 1–6C alkanoylamino radical; or $R^3$ and $R^7$ are joined to form, together with the N—C=N chain to which they are attached, a monocyclic or bicyclic heterocyclic ring system composed of 5- and/or 6-membered rings, which ring system may be partially unsaturated or fully unsaturated, which ring system may optionally include additional hetero atom selected from oxygen, nitrogen and sulphur atoms and which ring system may, where possible, carry one, two or three optional substituents selected from fluorine, chlorine and bromine atoms and 1–6C alkyl, 1–6C alkoxy, 1–6C alkylthio, trifluoromethyl, hydroxy, amino, 6–10C aryl, 7–11C arylalkyl, carboxy, 2–6C carboxyalkyl, 2–6C alkoxycarbonyl, 3–10C alkoxycarbonylalkyl, 1-6C hydroxyalkyl, heteroaryl-(1-6C)alkyl, furyl, thienyl, pyrrolyl, thiazolyl, oxazolyl, imidazolyl, thiadiazolyl, oxadiazolyl, triazolyl, pyrazolyl and pyrimidyl radicals;

or $R^3$ is a hydrogen atom or a 1-6C alkyl, 2-6C alkenyl or 2-6C alkynyl radical and $R^4$ is a carboxy radical; and wherein when $R^3$ is or contains a heteroaryl radical and when $R^3$ and $R^7$, when joined, is substituted by a heteroarylalkyl radical, that heteroaryl radical is a 5- or 6-membered heterocyclic ring which contains 1, 2, 3 or 4 heteroatoms selected from oxygen, nitrogen and sulphur atoms, such ring being optionally substituted by one or two substituents selected from methyl and amino radicals;

or $R^3$ and $R^7$ are joined to form, together with the N—C=N chain to which they are attached, a ring of the formula III:

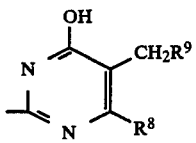

in which $R^8$ is a hydrogen atom or a 1-4C alkyl radical and $R^9$ is a furan-2-yl or thien-2-yl radical substituted in the 5-position, a phenyl radical substituted in the 3- or 4-position, a pyrid-3-yl radical substituted in the 5- or 6-position, a pyrid-4-yl radical substituted in the 2-position, or a pyrid-2-yl radical substituted in the 4- or 5-position, the substituent on $R^9$ being a radical of the formula IV:

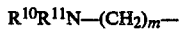

in which $R^{10}$ and $R^{11}$ are 1-4C alkyl radicals or $R^{10}$ and $R^{11}$ are joined to form, together with the nitrogen atom to which they are attached, a pyrrolidine, piperidine or morpholine ring and m is 1 to 4:

and the pharmaceutically-acceptable acid-addition salts thereof.

It is to be understood that, in the above formula I and throughout this specification, although the double bonds in both groups attached to ring X have been inserted in particular positions, other tautomeric forms are possible, and this invention includes such tautomeric forms within its scope, both in terms of the compounds of the invention and in terms of the manufacturing processes. Similarly, when $R^3$ and $R^7$ are joined to form a heterocyclic ring which is substituted by a hydroxy radical, that radical may exist in the tautomeric keto form. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a halogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for $R^1$ and $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on W is a methyl radical.

A particular value for $R^5$ is a hydrogen atom or a methyl radical.

A particular value for $R^6$ is a hydrogen atom or a methyl radical.

A particular value for the radical of the formula II is a 2-methoxyethyl, 2-hydroxyethyl, 2-methylthioethyl or 2-dimethylaminoethyl radical.

A particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring, each being optionally substituted, where possible, by one or two substituents selected from fluorine, chlorine and bromine atoms and methyl, methoxy, trifluoromethyl, hydroxy and amino radicals.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxypropyleneoxy, oxyethyleneoxymethylene, oxyethylenethio, oxypropylenethio, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethylene-ethynylenemethylene radical.

These values for —A— are written reading from left to right in formula I such that the first named part of the radical is attached to ring X and the last named part of the radical is attached to $C(R^4)=NR^3$. Thus, for example, when —A— is a thiotrimethylene radical, the compound of the formula I contains the part structure V:

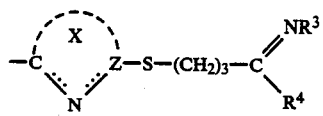

A particular value for $R^3$ is a hydrogen atom or a methyl, cyclohexyl, cyclobutylmethyl, 2,2,2-trifluoroethyl, 2-hydroxyethyl, 2-aminoethyl, 2-methylaminoethyl, 2-dimethylaminoethyl, 2-carboxyethyl, acetyl, benzoyl, phenyl, benzyl, allyl, propargyl, trifluoroacetyl, thioacetyl, thiobenzoyl, cyano, carbamoyl, thiocarbamoyl, methylcarbamoyl, dimethylcarbamoyl, methylthiocarbamoyl, dimethylthiocarbamoyl, carboxy, methoxycarbonyl, methoxythiocarbonyl, oxamoyl, sulphamoyl, methylsulphamoyl, dimethylsulphamoyl, phenylsulphamoyl, benzylsulphamoyl, methanesulphonyl, benzenesulphonyl, hydroxy, methoxy, amino, methylamino, dimethylamino, phenylamino, methoxycarbonylamino, phenoxycarbonylamino, acetylamino, benzoylamino, thioacetylamino, thiobenzoylamino, heteroarylcarbonylamino, heteroarylacetylamino, methanesulphonylamino, benzenesulphonylamino, ureido, thioureido, oxamoylamino, heteroaryl or heteroarylmethyl radical wherein the heteroaryl part is a furyl, thienyl, pyrrolyl, thiazoyl, oxazolyl, imidazolyl, thiadiazolyl, oxadiazolyl, triazolyl, pyrazolyl, pyridyl or pyrimidyl radical which is optionally substituted by one or two substituents selected from methyl and amino radicals.

A particular value for $R^4$ is a radical of the formula $NHR^7$ in which $R^7$ is a hydrogen atom or a methyl, allyl, propargyl, cyano, acetyl, carbamoyl, methylcarbamoyl or acetylamino radical. A further particular value for $R^4$ is a carboxy radical when $R^3$ is a hydrogen atom or a methyl, allyl or propargyl radical.

A particular value for the ring system formed when $R^3$ and $R^7$ are joined is an imidazole, imidazoline, triazole, pyrimidine, oxadiazole, thiadiazole, 1,3,5-triazine, 1,2,4-triazine, benzimidazole, quinazoline or purine (linked through the 2- or 8-position) ring system each of which ring systems may, where possible, carry one, two or three optional substituents selected from fluorine, chlorine and bromine atoms and methyl, ethyl, propyl, butyl, methoxy, methylthio, trifluoromethyl, hydroxy, amino, phenyl, benzyl, carboxymethyl, methoxycarbonyl, methoxycarbonylmethyl, hydroxymethyl, furyl, thienyl, pyrrolyl, thiazolyl, oxazolyl, imidazolyl, thiadiazolyl, oxadiazolyl, triazolyl, pyrazolyl and pyrimidyl radicals and heteroarylmethyl and 2-heteroarylethyl radicals in which the heteroaryl part is a furyl, thienyl, pyrrolyl, thiazolyl, oxazolyl, imidazolyl, thiadiazolyl, oxadiazolyl, triazolyl, pyrazolyl, pyridyl or pyrimidyl radical, each optionally substituted by one or two substituents selected from methyl and amino radicals.

A further particular value for the ring formed when $R^3$ and $R^7$ are joined is a ring of the formula III given above in which $R^8$ is a hydrogen atom or a methyl radical and $R^9$ is a furan-2-yl or thien-2-yl radical substituted in the 5-position, a phenyl radical substituted in the 3- or 4-position, a pyrid-3-yl radical substituted in the 5- or 6-position, a pyrid-4-yl radical substituted in the 2-position or a pyrid-2-yl radical substituted in the 4- or 5-position, the substituent on $R^9$ being a radical of the formula IV given above in which $R^{10}$ and $R^{11}$ are methyl radicals or are joined to form, together with the nitrogen atom to which they are attached, a pyrrolidine, piperidine or morpholine ring and m is 1 to 4, preferably 1.

The following are twelve preferred features of the guanidine derivative of the formula I. When any one of these features is taken, either singly or in combination, with the other general or particular features of the guanidine derivative of the formula I listed above, there are obtained preferred sub-groups of compounds within the above general definition.

1. $R^3$ is a cyano radical and $R^4$ is a radical of the formula $NHR^7$ in which $R^7$ is a hydrogen atom.
2. $R^3$ and $R^7$ are joined to form an optionally-substituted imidazole, triazole or pyrimidine ring.
3. $R^3$ and $R^7$ are joined to form an unsubstituted imidazole ring, a triazole ring substituted in the 5-position by a 1-6C alkyl radical or a pyrimidine ring substituted in the 4-position by a hydroxy radical and in the 5-position by a 1-6C alkyl radical.
4. $R^3$ and $R^7$ are joined to form a triazole ring substituted in the 5-position by a methyl radical or a pyrimidine ring substituted in the 4-position by a hydroxy radical and in the 5-position by a methyl or ethyl radical.
5. $R^2$ is a hydrogen atom and $R^1$ is a 2,2,2-trifluoroethyl or 2,2,3,3-tetrafluoropropyl radical.
6. Ring X carries no optional substituent.
7. Ring X is a pyrazole, 1,2,3-triazole, pyridine, or pyrimidine in which A is linked at the 2-position, ring.
8. —A— is a tetramethylene, pentamethylene, oxytrimethylene, oxytetramethylene, thiotrimethylene or thiotetramethylene radical.
9. —A— is a tetramethylene, oxytrimethylene or thiotrimethylene radical.
10. Ring X is a pyridine, or pyrimidine in which A is linked at the 2-position, ring and A is a thiotrimethylene radical.
11. Ring X is a pyrimidine ring in which A is linked at the 2-position and A is an oxytrimethylene radical.
12. Ring X is a pyrazole or 1,2,3-triazole ring and A is a tetramethylene radical.

Specific compounds of the invention are described in the Examples. The following is a preferred group of compounds:

3-methyl-5-(4-[3-(2-[2,2,2-trifluoroethyl]guanidino)-pyrazol-1-yl]butyl)-1,2,4-triazole (Example 7);

2-(4-[4-(2-[2,2,2-trifluoroethyl]guanidino)-1,2,3-triazol-2-yl]butyl)imidazole (Example 8);

4-hydroxy-5-methyl-2-(4-[4-(2-[2,2,2-trifluoroethyl]-guanidino)-1,2,3-triazol-2-yl]butyl)pyrimidine (Example 9);

5-methyl-3-(4-[4-(2-[2,2,3,3-tetrafluoropropyl]-guanidino)-1,2,3-triazol-2-yl]butyl)-1,2,4-triazole (Example 10);

4-hydroxy-5-methyl-2-(3-[2-(2-[2,2,2-trifluoroethyl]-guanidino)pyrid-6-ylthio]propyl)pyrimidine (Example 11);

4-hydroxy-5-methyl-2-(4-[4-(2-[2,2,2-trifluoroethyl]-guanidino)pyrimid-2-yl]butyl)pyrimidine (Example 12);

4-hydroxy-5-ethyl-2-(4-[4-(2-[2,2,2-trifluoroethyl]-guanidino)pyrimid-2-yl]butyl)pyrimidine (Example 42);

4-hydroxy-5-ethyl-2-(3-[4-(2-[2,2,2-trifluoroethyl]-guanidino)pyrimid-2-yloxy]propyl)pyrimidine (Example 59);

4-hydroxy-5-methyl-2-(4-[3-(2-[2,2,2-trifluoroethyl]-guanidino)pyrazol-1-yl]butyl)pyrimidine (Example 61);

3-methyl-5-(3-[4-(2-[2,2,2-trifluoroethyl]guanidino)-pyrimid-2-ylthio]propyl)-1,2,4-triazole (Example 88);

3-methyl-5-(3-[4-(2-[2,2,3,3-tetrafluoropropyl]-guanidino)pyrimid-2-ylthio]propyl)-1,2,4-triazole (Example 90);

3-methyl-5-(4-[4-(2-[2,2,2-trifluoroethyl]-guanidino)1,2,3-triazol-2-yl]butyl)-1,2,4-triazole (Example 103);

N-cyano-4-[3-(2-[2,2,2-trifluoroethyl]guanidino)-pyrazol-1-yl]butanamidine (Example 135);

N-cyano-4-[4-(2-[2,2,2-trifluoroethyl]guanidino)-1,2,3-triazol-2-yl]butanamidine (Example 137);

and the pharmaceutically-acceptable acid-addition salts thereof.

Of this group the compounds of Examples 7, 9, 10 and 61 are particularly preferred.

A suitable pharmaceutically-acceptable acid-addition salt of the guanidine derivative of the invention is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, $R^4$, A and ring X having the meanings stated above, unless indicated otherwise, are therefore provided as further features of the invention.

The process of the invention is characterised by:

(a) for those compounds in which $R^4$ is a radical of the formula $NHR^7$ and $R^3$ and $R^7$ are not joined, reaction of a compound of the formula VI:

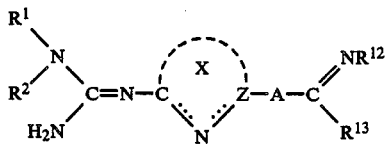

VI in which $R^{12}$ has one of the values given above for $R^3$ or $R^7$ and $R^{13}$ is a displaceable radical with a compound of the formula VII:

VII in which $R^{14}$ has one of the values given above for $R^7$ or $R^3$ respectively. When $R^{14}$ is a hydrogen atom, that is the compound of the formula VII is ammonia, it is convenient to use it in the form of a salt such as ammonium chloride. $R^{13}$ may, for example, be a 1-6C alkoxy radical, for example a methoxy or ethoxy radical. The reaction may be carried out in a diluent or solvent, for example methanol or ethanol. The reaction generally proceeds an ambient temperature, but may, in certain instances, require acceleration or completion by the application of heat, for example by heating to the boiling point of the diluent or solvent.

(b) for those compounds in which $R^4$ is a radical of the formula $NHR^7$ in which $R^3$ and $R^7$ are joined to form a heterocyclic ring system, reaction of a compound of the formula VIII:

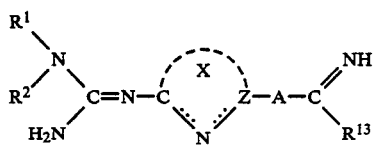

VIII in which $R^{13}$ is a displaceable radical, with a compound containing a 2-, 3- or 4-atom chain, two adjacent members of which may be incorporated into a 5- or 6-membered carbocyclic or heterocyclic ring, and in which the chain is functionalised in such a way that a cyclised amidine is formed. $R^{13}$ may, for example be an amino or 1-6C alkoxy, for example methoxy or ethoxy, radical. The following examples illustrate this general reaction for specific ring systems. When the ring to be formed is a optionally-substituted imidazole ring, the compound of the formula VIII in which $R^{13}$ is a displaceable radical is reacted with a compound of the formula IX:

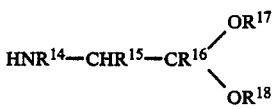

IX in which $R^{14}$, $R^{15}$ and $R^{16}$ are hydrogen atoms or the optional substituents on the heterocyclic ring system and $R^{17}$ and $R^{18}$ are 1-6C alkyl, for example methyl or ethyl, radicals, or $R^{17}$ and $R^{18}$ are joined to form an ethylene or propylene radical, for example as illustrated in Examples 3, 8, 34, 111 to 120 inclusive, and 123. When the ring to be formed is an optionally-substituted 1-imidazoline ring, the compound of the formula VIII in which $R^{13}$ is a displaceable radical is reacted with a compound of the formula X:

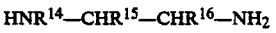

X in which $R^{14}$, $R^{15}$ and $R^{16}$ have the meanings given above, for example as illustrated in Example 16. When the ring to be formed is an optionally-substituted pyrimidine ring which carries a hydroxy radical in the 4-position, the compound of the formula VIII in which $R^{13}$ is an amino radical is reacted with a compound of the formula XI:

XI in which $R^{15}$, $R^{16}$ and $R^{17}$ have the meanings given above, for example as illustrated in Examples 5, 9, 11, 12, 23, 24, 29, 32 and 35-66 inclusive. When the ring to be formed is a pyrimidine ring which carries an amino radical in the 4-position, the compound of the formula VIII in which $R^{13}$ is an amino radical is reacted with 2-chloroacrylonitrile. The process of the invention may be conducted in a diluent or solvent, such as methanol or ethanol, and be accelerated or completed by the application of heat, for example by heating to the boiling point of the diluent or solvent. When using the compound of the formula IX the reaction may conveniently be conducted in two stages, the second stage being initiated by the addition of a mineral acid, for example HCl. When using 2-chloroacrylonitrile as starting material, the reaction may be conducted in the presence of triethylamine.

(c) for those compounds in which $R^4$ is a radical of the formula $NHR^7$ in which $R^3$ and $R^7$ are joined to form a 1,2,4-triazole ring substituted in the 5-position by an alkyl, trifluoromethyl, hydroxy, aryl, arylalkyl, carboxyalkyl, alkoxycarbonylalkyl, hydroxyalkyl, heteroarylalkyl, furyl, thienyl, pyrrolyl, thiazolyl, oxazolyl, imidazolyl, thiadiazolyl, oxadiazolyl, triazolyl, pyrazolyl or pyrimidyl radical, cyclisation of the compound of the formula XII:

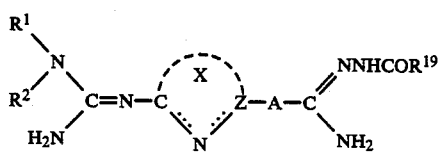

XII in which $R^{19}$ is a 1-6C alkyl, trifluoromethyl, hydroxy, 1-6C alkoxy, 6-10C aryl, 7-11C arylalkyl, 2-6C carboxyalkyl, 2-6C alkoxycarbonyl, 3-10C alkoxycarbonylalkyl, 1-6C hydroxyalkyl, heteroaryl-(1-6C)-alkyl, furyl, thienyl, pyrrolyl, thiazolyl, oxazolyl, imidazolyl, thiadiazolyl, oxadiazolyl, triazolyl, pyrazolyl or pyrimidyl radical. The process may be carried out by heating the compound of the formula XII in the absence of a diluent or solvent, for example at a temperature of between 50° and 200° C. Alternatively, the process may be conducted in a diluent or solvent, for example ethanol, at the boiling point of the diluent or solvent.

(d) for those compounds in which $R^3$ is a carbamoyl radical, hydrolysis of the corresponding compound in which $R^3$ is a cyano radical. The process may, for example, be carried out in an alcoholic diluent or solvent such as methanol or ethanol, or mixtures of these with chloroform, containing dissolved HCl gas, and in the presence of at least one equivalent of water.

(e) for those compounds in which the group inserted into A is an oxygen or sulphur atom or an NH or N-alkyl radical, reaction of a compound of the formula XIII or XIV:

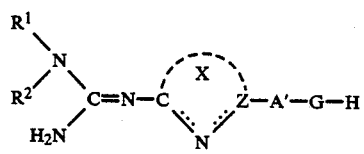

XIII

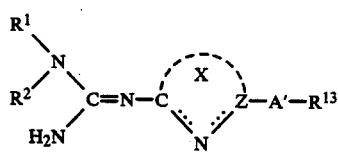

XIV with a compound of the formula XV or XVI respectively:

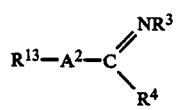 XV

 XVI in which G is an oxygen or sulphur atom or an NH or N-alkyl radical, $R^{13}$ is a displaceable radical and $A^1$ and $A^2$ are fragments of A, including direct bonds, and are such that $A^1—G—A^2$ falls within the general definition of A given above. $R^{13}$ is, for example, a halogen atom, for example a chlorine, bromine or iodine atom. When $R^{13}$ is directly attached to ring X, $R^{13}$ may, for example, be a methylsulphinyl or methylsulphonyl radical. The process may be conducted in a diluent or solvent, for example t-butanol, and the reaction may be accelerated or completed by the application of heat, for example by heating to the boiling point of the diluent or solvent. When G is an oxygen or sulphur atom it is advantageous to conduct the reaction in the presence of a base. When the diluent or solvent is t-butanol, the base may be sodium t-butoxide.

(f) for those compounds in which $R^4$ is a radical of the formula $NHR^7$ in which $R^7$ is a hydrogen atom, reaction of a compound of the formula XVII:

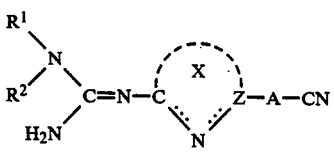 XVII with a compound of the formula XVIII:

$R^3—NH_2$ XVIII

The reaction may be conducted in a diluent or solvent, for example n-propanol or t-butanol, and may be accelerated or completed by the application of heat, for example by heating to the boiling point of the diluent or solvent.

(g) for those compounds in which Z is a nitrogen atom, reaction of a compound of the formula XIX:

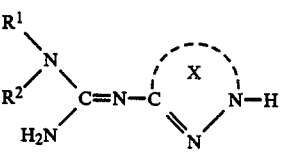 XIX with a compound of the formula XX:

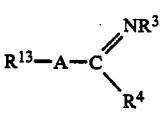 XX in which $R^{13}$ is a displaceable radical. $R^{13}$ is, for example, a halogen atom, for example a chlorine, bromine or iodine atom.

(h) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms, each of which carries different substitutents. The appropriate amine for use in this reaction may therefore be ammonia, an amine of the formula $R^1R^2NH$ or an amine of the formula XXI:

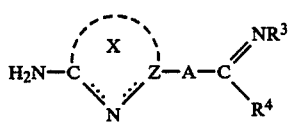
XXI

The reaction may be conducted in a diluent or solvent such as methanol or ethanol. In many cases it is advantageous to use a catalyst such as lead oxide, mercuric oxide or sodium hypochlorite. The reaction may be conducted at ambient temperature or it may be accelerated or completed by the application of heat, for example by heating to the boiling point of the diluent or solvent.

(i) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1R^2NH$ or of the formula XXI given above.

(j) for those compounds in which $R^4$ is a radical of the formula $NHR^7$ in which $R^3$ and $R^7$ are joined to form a 1,2,4-triazole ring substituted in the 5-position by an amino or hydroxy radical, or a 1,3,5-triazine ring substituted in the 4-position by an amino or hydroxy radical and in the 6-position by a hydrogen atom or an alkyl, trifluoromethyl, aryl, arylalkyl, alkoxycarbonylalkyl, hydroxyalkyl, heteroarylalkyl, furyl, thienyl, pyrrolyl, thiazolyl, oxazolyl, imidazolyl, thiadiazolyl, oxadiazolyl, triazolyl, pyrazolyl, or pyrimidyl radical, reaction of a compound of the formula XXII:

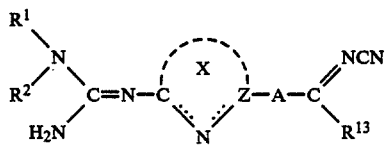
XXII in which $R^{13}$ is a displaceable radical with hydrazine or with a compound of the formula XXIII:

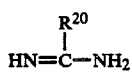
XXIII respectively in which $R^{20}$ is a hydrogen atom or a 1–6C alkyl, trifluoromethyl, 6–10C aryl, 7–11C arylalkyl, 2–6C alkoxycarbonylalkyl, 1–6C hydroxyalkyl, heteroaryl-(1–6C)alkyl, furyl, thienyl, pyrrolyl, thiazolyl, oxazolyl, imidazolyl, thiadiazolyl, oxadiazolyl, triazolyl, pyrazolyl or pyrimidyl radical, whereafter, if desired, the amino radical on the 1,2,4-triazole or 1,3,5-triazine ring so formed is transformed to a hydroxy radical by standard methods.

$R^{13}$ may, for example, be a 1–6C alkoxy radical, for example a methoxy radical. The subsequent transformation of amino radical to hydroxy radical may be carried out, for example, by hydrolysis or by diazotisation followed by hydrolysis.

(k) for those compounds in which ring X is a thiazole ring, reaction of a compound of the formula XXIV:

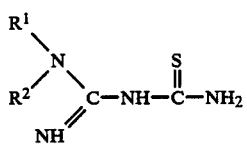
XXIV with a compound of the formula XXV:

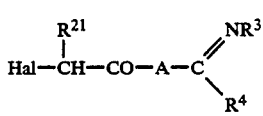
XXV in which Hal is a chlorine or bromine atom and $R^{21}$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

A critical intermediate for preparing the starting materials for several of the processes of the invention is the starting material of the formula XVII for use in process (f). This starting material may be prepared by separate construction of the two side chains on the appropriate ring X. Thus the left hand side chain may be constructed by reduction of a nitro group to an amino group, reaction of this amino group with an isothiocyanate of the formula $R^1R^2N=C=S$;, and finally reaction of the resulting thiourea with ammonia in the presence of mercuric oxide. The method of construction of the right hand side chain may vary depending on the nature of ring X, the nature of the atom in ring X to which A is attached (carbon or nitrogen) and the presence or absence of inserted atoms or groups in chain A. When A contains no inserted group, or the inserted group is a phenylene radical and Z is a carbon atom, it is preferable to construct ring X with the right hand side chain already in place. Thus, for example, when ring X is a pyrimidine ring, it may be formed by reaction of a suitably substituted amidine with 2-chloroacrylonitrile to give the corresponding 4-aminopyrimidine derivative, for example as illustrated in Examples 12 and 21. When the inserted group in A is a cycloalkylene radical, the chain A may be constructed by a conjugate addition to the corresponding cycloalk-2-enone. When the inserted group in A is a vinylene or ethynylene radical, A may be introduced by formation of the double or triple bond by standard coupling methods. When the inserted group in A is an oxygen or sulphur atom or an NH or N-alkyl radical, the right hand side chain may be built up by a method similar to that in process (e), for example as illustrated in Examples 1, 2, 11, 24, 32 and 34. When Z is a nitrogen atom, the right hand chain may be formed by a method similar to that in process (g), for example as illustrated in Example 6, 8, 27 and 29.

The starting material of the formula VI for use in process (a) in which $R^{12}$ is a hydrogen atom and $R^{13}$ is an alkoxy radical, or of the formula VIII for use in process (b) in which R[13] is an alkoxy radical, may be prepared from the starting material of the formula XVII by treatment with anhydrous HCl in a diluent or solvent of the formula R[13]—OH, for example as illustrated in Examples 1, 3, 4, 6, 8, 10, 11, 12, 13, 21, 23, 24, 26, 29, 32 and 34.

The starting material of the formula XII for use in process (c) may be prepared from the starting material of the formula VIII in which R[13] is a displaceable radical by reaction with a compound of the formula XXVI:

  XXVI

The starting material of the formula XIII or XIV for use in process (e) and the starting material of the formula XIX for use in process (g) may be prepared by construction of the substituted guanidine radical on a suitably-substituted ring X.

The starting material of the formula XXI for use in process (h) or (i) may be prepared by the methods described above for the preparation of compounds of the formula VI or VIII in which the right hand chain is constructed first, followed by use of one of the processes (a) or (b).

The cyanamide corresponding to the amine of the formula XXI for use in process (i) may be prepared by reaction of the compound of the formula XXI with cyanogen bromide.

The starting material of the formula XXII for use in process (j) may be prepared by reaction of the compound of the formula VI in which R[12] is a hydrogen atom and the nitrogen to which it is attached is in the protonated form with cyanamide.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced uptake of aminopyrine into the acid space of parietal cells.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$, 5% $CO_2$) Krebs-Henseleit buffer (pH 7.4). The tissue is allowed to stabilize over 1 hour during which time it is washed 2-4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

The aminopyrine test is carried out as follows:

Gastric mucosa from the New Zealand white rabbit is removed from the underlying muscle and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serum albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40-60 minutes. Any remaining large pieces of tissue are removed by filtration through nylon mesh. The mixture of glands and cells is collected by centrifugation at 200×g. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. net weight of tissue]. The tissue suspension is stirred under an oxygen atmosphere at 32° C. for at least 1 hour before use. The tissue suspension is incubated with the test compound and aminopyrine (10 $\mu$M) labelled with $C^{14}$ on the dimethylamino group (0.1 $\mu$Ci/ml.) for 20 minutes. The uptake of the aminopyrine is then stimulated by addition of histamine and the phosphodiesterase inhibitor ICI 63197 (*Biochem. Soc. Special Publication* 1, 1973,. pp 127–132) to final concentrations of $10^{-5}$M. and $5\times10^{-7}$M. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested either on the guinea pig atrium test or on the aminopyrine test. All those tested on the guinea pig atrium test are active at or below a bath concentration of 10 $\mu$M. and the more active compounds show complete inhibition of response at this concentration. All those tested on the aminopyrine test gave a 50% inhibition of uptake of aminopyrine at or below a concentration of 3 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats or dogs provided with gastric fistulae or denervated fundic pouches, and whose gastric secretion is stimulated by administration of a secretagogue, for example histamine, pentagastrin, bethanechol or food.

The test in rats is carried out as follows:

Female rats (200-230 g.) are anesthetized by intramuscular administration of urethane (1.5 g/kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compounds is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO <2%).

The test in dogs provided with chronic fistulae is carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 μmol./kg/hour of histamine or 2 μg/kg./hour pentagastrin) in saline (15 ml./hour) is begun. Gastric acid samples are collected every 15 minutes. The volume of each sample is measured and a 1 ml. aliquot is titrated to neutrality with 100 mM NaOH to determine acid concentration. When a plateau of secretion is reached (1-2 hours), the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes of ascertained and the test compound, contained in 25 ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is re-opened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route it is administered in a gelatin capsule with 15 ml. of water. One hour later, the fistula is opened and intravenous infusion of the secretagogue is immediately begun. Gastric acid samples are measured as above and the approach of acid secretion to a plateau is compared to that of an undosed control animal.

The test in dogs provided with denervated fundic pouches is carried out as follows:

Male beagle dogs (14-22 kg.) are prepared with vagally denervated pouches of the fundic gland area by the method of Rudick et al. (J. Surg. Res. 1967, 7 383.) The animals are allowed 4-6 weeks to recover from surgery and a further period of 2-3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 μg./minute. This dose of agonist produces a submaximal (60-90% of maximum) increase in acid output in all dogs used. Pouch secretions are collected over 15 minute periods into graduated glass test-tubes and the volume measured to the nearest 0.1 ml. A 500 μl sample is diluted with 5 ml. of saline and titrated to pH 7.0 with 100 mM. NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the atrium and aminopyrine tests are predictive of activity in the rat and dog tests.

No overt toxicity or side effects were noted during the rat or dog tests. The compounds 3-methyl-5-(4-[3-(2-[2,2,2-trifluoroethyl]guanidino)pyrazol-1-yl]butyl)-1,2,4-triazole, 4-hydroxy-5-methyl-2-(4-[4-(2-[2,2,2-trifluoroethyl]guanidino)-1,2,3-triazol-2-yl]butyl)pyrimidine, 5-methyl-3-(4-[4-(2-[2,2,3,3-tetrafluoropropyl]guanidino)-1,2,3-triazol-2-yl]butyl)-1,2,4-triazole, 4-hydroxy-5-methyl-2-(3-[2-(2-[2,2,2-trifluoroethyl]guanidino)pyrid-6-ylthio]propyl)pyrimidine and 4-hydroxy-5-methyl-2-[4-(4-[2-(2,2,2-trifluoroethyl)guanidino]pyrimid-2-yl)butyl]pyrimidine were administered intravenously to groups of two anaesthetised rats and four conscious mice at doses which were respectively ten times and one hundred times the dose, in mg./kg., which produced an approximate 50% inhibition of gastric secretion in the anaesthetised rat. No toxic symptoms were noted in any of the dosed animals.

A number of compounds exemplified in this specification exhibit inhibition of acid secretion which shows little or no decline from peak inhibition for several hours.

The N-methylcyanoguanidine group in known H-2 receptor antagonists is potentially changeable into the mutagenic N-nitroso N-methylcyanoguanidine group in the mammalian body (Pool et al., Toxicology, 1979, 15, 69). The corresponding group in the compounds of the present invention, $C(R^4)=NR^3$, is resistant to reaction with nitrous acid over the pH range 1-4 (Baum et al., J. Chem. Research (S), 1980, 212-213) when $R^4$ is $NHR^7$ and $R^3$ and $R^7$ are joined to form a triazole, imidazole or 4-hydroxypyrimidine ring.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or aspirin, prostaglandins, for example 16,16-dimethylprostaglandin $E_2$; classical anti-histamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1-10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 5 mg. and 500 mg., and preferably between 10 mg. and 100 mg., of guanidine derivative or an intravenous, subcutaneous or intramuscular dose of between 0.5 mg. and 50 mg., and preferably between 2 mg. and 20 mg., of the guanidine derivative, the composition being administered 1 to 4 times, and preferably once, per day. The rectal dose will be approximately the same as the oral dose. The composition may be administered less frequently when it contains an amount of guanidine derivative which is a multiple of the amount which is effective when given 1-4 times per day.

The invention is illustrated, but not limited, by the following Examples. The n.m.r. spectra are quoted in $\delta$ relative to tetramethylsilane ($\delta=0$) as internal standard (s=singlet, d=doublet, t=triplet, q=quartet, m=multiplet, br=broad). The temperatures are in degrees Centigrade. The following contractions are used:
HOAc=acetic acid
DMF=dimethyl formamide
ether=diethyl ether
DMSO=dimethylsulphoxide
MeOH=methanol
EtOH=ethanol
THF=tetrahydrofuran
EtOAc=ethyl acetate Attention is drawn to the fact that 3-nitropyrazole (Example 6,) and 4-nitrotriazole (Example 8) are both explosion hazards.

EXAMPLE 1

A solution of 4-[4-(2-[2,2,2-trifluoroethyl]guanidino)-pyrimid-2-ylthio]butyronitrile (0.65 g.) in MeOH (15 ml.) and ether (30 ml.) at 0° was saturated with HCl gas, and then left at 0° for 18 hours. The solution was evaporated to dryness and the residue of the imino-ether treated with a solution of sodium methoxide (0.22 g.) n MeOH (10 ml.). A mixture of hydroxylamine hydrochloride (0.21 g.), MeOH (10 ml.) and sodium methoxide (0.16 g.) was added and the mixture stirred at room temperature for 3 hours and then evaporated to dryness. The residue was partitioned between water and EtOAc, and the EtOAc dried and evaporated to dryness. The residue was purified by preparative t.l.c. on Merck GF 254 plates using EtOAc/MeOH/ammonia (s.g. 0.88) 6:1:0.5 v/v/v as developing solvent to give 4-[4-(2-[2,2,2-trifluoroethyl]guanidino)pyrimid-2-ylthio]-1-oximinobutylamine (0.48 g.) characterised as the bis hydrogen maleate, m.p. 137-139°.

The starting material for use in the above process may be prepared as follows:

4-Chlorobutyronitrile (0.23 g.) in EtOH (2 ml.) was added to a solution of 2-thiocytosine (0.25 g.) in 0.5 N aqueous NaOH (5 ml.) and the mixture stirred for 18 hours. A further portion of 4-chlorobutyronitrile (0.23 g.) was added and the mixture stirred a further 24 hours. The solution was concentrated in vacuo to 2 ml. and cooled and the crystalline precipitate collected to give 4-[4-aminopyrimid-2-ylthio]butyronitrile (0.3 g.), m.p. 99-100°.

A mixture of 4-[4-aminopyrimid-2-ylthio]butyronitrile (0.25 g.), acetonitrile (3 ml.) and 2,2,2-trifluoroethylisothiocyanate (0.21 g.) was stirred at 70° for 72 hours and then evaporated to dryness. The residue was crystallised from a mixture of ether and petroleum ether (b.p. 60°-80°) to give 4-[4-(3-[2,2,2-trifluoroethyl]thioureido)pyrimid-2-ylthio]butyronitrile (0.37 g.), m.p. 125°-126°.

A mixture of 4-[4-(3-[2,2,2-trifluoroethyl]thioureido)-pyrimid-2-ylthio]butyronitrile (0.32 g.), saturated ethanol ammonia (20 ml.) and yellow mercuric oxide (0.5 g.) was stirred at room temperature for 20 hours and then filtered and the filtrate evaporated to dryness. The residue was recrystallised from a mixture of acetone and petroleum ether (b.p. 60°-80°) to give 4-[4-(2-[2,2,2-trifluoroethyl]guanidino)pyrimid-2-ylthio]butyronitrile (0.29 g.), m.p. 137°.

EXAMPLE 2

A mixture of 6-[4-(2-[2,2,2-trifluoroethyl]guanidino)-pyrimid-2-ylthio]hexanenitrile (173 mg.), hydroxylamine hydrochloride (35 mg.), $K_2CO_3$ (70 mg.) and n-propanol (5 ml.) was heated under reflux on the steam bath for 4 hours. More hydroxylamine hydrochloride (70 mg.) and $K_2CO_3$ (140 mg.) were added and the mixture heated under reflux for a further 18 hours and then evaporated to dryness. The residue was dissolved in 1N HCl and the solution washed with EtOAc and then basified with 10N NaOH. The mixture was extracted with EtOAc and the extract dried and evaporated to dryness. A solution of the residue in EtOAc was added to a solution of maleic acid in acetone and the precipitated salt collected and recrystallised from EtOH to give 6-[4-(2-[2,2,2-trifluoroethyl]guanidino)-pyrimid-2-ylthio]-1-oximinohexylamine bis hydrogen maleate (75 mg.), m.p. 156°–158° (decomp.).

The starting material for use in the above process may be prepared in an analogous manner to that described for the butyronitrile in Example 1.

EXAMPLE 3

To a mixture of 4-[4-(2-[2,2,2-trifluoroethyl]guanido)-pyrimid-2-ylthio]butyronitrile (1 g.) in MeOH (5 ml.) and CHCl$_3$ (5 ml.) at 0° was added dry HCl gas until the mixture was saturated. The resulting solution was allowed to stand at 0° for 2 days and then evaporated to dryness. To the residue of the imino-ether in MeOH (5 ml.) was added aminoacetaldehyde dimethyl acetal (0.7 g.). The mixture was allowed to stand at room temperature 7 days and then concentrated HCl (15 ml.) added. The mixture was then heated at 90° for 15 minutes and then evaporated to dryness. The residue was dissolved in water (20 ml.) and the mixture basified with aqueous NaOH. The aqueous mixture was extracted with EtOAc (2×20 ml.) and the organic layers evaporated to dryness. The residue was then purified by medium pressure liquid chromatography on silica using CHCl$_3$/MeOH/aqueous ammonia (s.g. 0.880) 15:1:0.05 v/v/v as eluant. The appropriate fraction was evaporated and the residue, treated in acetone with maleic acid, gave 0.085 g. of 2-(3-[4-(2-[2,2,2-trifluoroethyl]-guanidino)pyrimid-2-ylthio]propyl)imidazole dihydrogen maleate, m.p. 168°–169°.

EXAMPLE 4

To a mixture of 4-[4-(2-[2,2,2-trifluoroethyl]-guanidino)pyrimid-2-ylthio]butyronitrile (1.5 g.) in MeOH (10 ml.) and CHCl$_3$ (20 ml.) at 0° was added dry hydrogen chloride gas until the mixture was saturated. The solution was allowed to stand at 0° for 2 days and then evaporated to dryness. The residue was partitioned between a solution of K$_2$CO$_3$ (5 g.) in water (25 ml.) and CHCl$_3$ (3×25 ml.). The combined CHCl$_3$ extracts were then evaporated to dryness and to the residue of the imino-ether in MeOH (5 ml.) was added ammonium chloride (0.25 g.). After stirring the mixture at ambient temperature for 2 hours the mixture was evaporated to dryness and the residue triturated with ether to give 4-[4-(2-[2,2,2-trifluoroethyl]guanidino)pyrimid-2-ylthio]butanamidine hydrochloride having the following n.m.r. in d$_6$DMSO:

9.1 (bs, 2H), 8.8 (bs, 2H), 8.1 (d, 1H), 6.4 (d, 1H), 4.2 (q, 2H), 3.1 (t, 2H), 2.5 (m; includes DMSO), 2.08 (m, 2H).

EXAMPLE 5

To a mixture of ethyl acetoacetate (0.3 g.) and sodium hydride (50% w/w dispersion in oil; 0.12 g.) in MeOH (8ml.) was added 4-[4-(2-[2,2,2-trifluoroethyl]-guanidino)pyrimid-2-ylthio]butanamidine hydrochloride (0.7 g.), the mixture heated under reflux overnight and then evaporated to dryness. The residue was purified by medium pressure liquid chromatography on silica using CHCl$_3$/MeOH/aqueous ammonia (s.g. 0.880) 9:1:0.1 v/v/v as eluant. The appropriate fraction was evaporated and the residue recrystallised from acetonitrile to give 0.19 g. of 4-hydroxy-6-methyl-2-(3-[4-(2-[2,2,2-trifluoroethyl]guanidino)pyrimid-2-ylthio]-propyl)pyrimidine, m.p. 200°–202°.

EXAMPLE 6

A solution of 5-[3-(2-[2,2,2-trifluroethyl]guanidino)-pyrazol-1-yl]valeronitrile (0.94 g.) in chloroform (10 ml.) and MeOH (10 ml.) at 0° was saturated with HCl gas. The mixture was kept at 5° for 24 hours then volatile material was evaporated in vacuo at 40°. The resulting syrup was cooled in ice and treated with ice-cold aqueous potassium carbonate solution (50 ml. of 10% w/v). The resulting oily precipitate was extracted with chloroform, dried (MgSO$_4$) and evaporated in vacuo to give the iminoether as an oil. This imino ether (0.5 g.) was dissolved in MeOH (5 ml.) and acethydrazide (0.173 g.) was added. The resulting solution was kept at 20° for 48 hours then volatile material was evaporated in vacuo to give a syrup which crystallised upon trituration with ether/EtOH (9:1 v/v) to give N-acetylamino-5-[3-(2-[2,2,2-trifluoroethyl]guanidinopyrazol-1-yl]valeramidine, m.p. 142°–144°.

The starting material may be prepared as follows:

Sodium hydride paste (6.16 g. of 61% w/w suspension in liquid paraffin) was added portionwise over 30 minutes to a solution of 3-nitropyrazole (17.4 g.) in dry DMF (150 ml.) with external ice cooling to maintain the temperature at 20°–30°. The mixture was stirred for 45 minutes and to the almost clear solution was added 5-bromovaleronitrile (25 g.) over 30 minutes, at 25°–30°, and the mixture was stirred for 4 hours. Water (450 ml.) and EtOAc (450 ml.) were added and the upper layer was separated, dried (MgSO$_4$) and evaporated in vacuo to an oil which was a mixture of 5-(3-nitro-pyrazol-1-yl)valeronitrile and 5-(5-nitropyrazol-1-yl)valeronitrile. The oil was divided into two 15 g. portions which were fractionated on a silica column (3.5 cm diameter × 100 cm long) eluted at 2 atmospheres by EtOAc/60°–80° petroluem ether (3:7 v/v). The 1,5 isomer was eluted first followed by the 1,3 isomer. The 5-(3-nitropyrazol-1-yl)valeronitrile had m.p. 32°–33°.

To a solution of 5-(3-nitropyrazol-1-yl)valeronitrile (9.16 g.) in dry THF (200 ml.) was added 5% w/w palladium on carbon (1.8 g.). The mixture was stirred at 20° under an atmosphere of hydrogen. 3.2 Liters of hydrogen were absorbed over 4 hours. The catalyst was filtered off and the filtrate was evaporated in vacuo to give 5-(3-aminopyrazol-1-yl)valeronitrile as an oil.

To a solution of 5-(3-aminopyrazol-1-yl)valeronitrile (7.0 g.) in acetonitrile (25 ml.) was added 2,2,2-trifluoro-ethylisothiocyanate (6.02 g.). After 15 minutes the solvent was evaporated in vacuo to give 5-(3-[3-(2,2,2-trifluoroethyl)thioureido]pyrazol-1-yl)valeronitrile as a white crystalline solid, m.p. 96°–98°.

The above thiourea (12.5 g.) was dissolved in 8 M ammonia in EtOH (120 ml.). Mercuric oxide (12.8 g.) was added and the mixture was stirred at 20° for 30 minutes. The resulting mixture was filtered and the filtrate was evaporated in vacuo to give 5-[3-(2-[2,2,2-trifluoroethyl]guanidino)pyrazol-1-yl]valeronitrile as an oil. A sample of the oil was dissolved in acetone and 5 molecular equivalents of maleic acid were added. Ether was added to the resulting clear solution to produce the crystalline maleate, m.p. 123°–125°.

EXAMPLE 7

N-acetylamino-5-[3-(2-[2,2,2-trifluoroethyl]-guanidino)pyrazol-1-yl]valeramidine (0.141 g.) was heated at 160° for 12 minutes. The resulting glass was dissolved in acetone (1 ml.) containing maleic acid (0.056 g.). Upon addition of ether the dimaleate salt of 3-methyl-5-(4-[3-(2-[2,2,2-trifluoroethyl]guanidino)-pyrazol-1-yl]butyl)-1,2,4-triazole, m.p. 125°–130°, crystallised out.

EXAMPLE 8

A solution of unpurified methyl 5-[4-(2-[2,2,2-trifluoroethyl]guanidino)-1,2,3-triazol-2-yl]valerimidate (0.5 g.) and aminoacetaldehyde dimethyl acetal (0.2 ml.) in MeOH (10 ml.) was stirred at room temperature overnight. The mixture was evaporated to dryness, the residue dissolved in concentrated aqueous HCl (10 ml.) and the mixture heated on a steam bath for 10 minutes. The mixture was evaporated, the residue basified with saturated aqueous NaHCO$_3$ solution and extracted with EtOAc. This extract was extracted with 2N aqueous HCl, the acid extract was basified with 2.5N aqueous NaOH and extracted with EtOAc. This extract was dried (MgSO$_4$), concentrated to a small volume, and treated with a solution of maleic acid (0.36 g.) in a small volume of acetone to give 0.35 g. of 2-(4-[4-(2-[2,2,2-trifluoroethyl]guanidino)-1,2,3-triazol-2-yl]butyl)imidazole dihydrogen maleate, m.p. 137°–139°.

The starting material may be obtained as follows:

A stirred solution of 4-nitro-1,2,3-triazole (23.0 g.) in dry DMF (135 ml.) was treated at room temperature with a dispersion of sodium hydride (4.8 g.) in mineral oil (4.8 g.). The mixture was stirred for 30 minutes and then treated with 5-bromovaleronitrile (33.0 g.). The mixture was stirred overnight at room temperature and then poured into water. The product was extracted into EtOAc and purified by column chromatography on silica gel (1 kg.) eluted with EtOAc/petroleum ether (b.p. 60°–80°) (1:1 v/v) to give 22.3 g. of 5-(4-nitro-1,2,3-triazol-2-yl)valeronitrile as an oil.

A suspension of palladium on charcoal (5% w/w; 0.5 g.) in a solution of 5-(4-nitro-1,2,3-triazol-2-yl)valeronitrile (1.0 g.) in HOAc (20 ml.) was stirred under one atmosphere of hydrogen until 420 ml. of hydrogen had been absorbed. The mixture was filtered and evaporated to give 0.85 g. of 5-(4-amino-1,2,3-triazol-2-yl)valeronitrile as an oil.

A solution of 5-(4-amino-1,2,3-triazol-2-yl)valeronitrile (0.35 g.) and 2,2,2-trifluoroethylisothiocyanate (0.50 g.) in acetonitrile (5 ml.) was stirred at room temperature overnight. The mixture was evaporated and the residue recrystallised from toluene/petroleum ether (b.p. 60°–80°) to give 0.50 g. of 5-[4-(3-[2,2,2-trifluoroethyl]trioureido)-1,2,3-triazol-2-yl]valeronitrile, m.p. 86°–88° after recrystallisation from toluene.

A stirred solution of 5-[4-(3-[2,2,2-trifluoroethyl]thioureido)-1,2,3-triazol-2-yl]valeronitrile (0.45 g.) in ammoniacal EtOH (6M; 10 ml.) was treated at room temperature with mercuric oxide (0.6 g.). The mixture was stirred at room temperature for 2 hours. The mixture was filtered and evaporated to give 0.41 g. of 5-[4-(2-[2,2,2-trifluoroethyl]guanidino)-1,2,3-triazol-2-yl]valeronitrile.

A solution of unpurified 5-[4-(2-[2,2,2-trifluoroethyl]guanidino)-1,2,3-triazol-2-yl]valeronitrile (1.0 g.) in a mixture of CHCl$_3$ (15 ml.) and MeOH (10 ml.) was saturated at 0° with hydrogen chloride gas. The mixture was maintained at 5° for 2 days in a sealed flask. The mixture was evaporated to dryness to give the product as a hydrochloride salt. The hydrochloride salt was basified with saturated aqueous NaHCO$_3$ solution and the mixture extracted with CH$_2$Cl$_2$. The extract was dried (MgSO$_4$) and evaporated to give 1.0 g. of methyl 5-[4-(2-[2,2,2-trifluoroethyl]guanidino)-1,2,3-triazol-2-yl]valerimidate as an oil which was used without further purification.

EXAMPLE 9

A mixture of methyl 5-[4-(2-[2,2,2-trifluoroethyl]guanidino)-1,2,3-triazol-2-yl]valerimidate (1.0 g.) and ammonium chloride (0.18 g.) in MeOH (15 ml.) was stirred for 18 hours at room temperature. The mixture was evaporated to dryness to give 1.0 g. of unpurified 5-[4-(2-[2,2,2-trifluoroethyl]guanidino)-1,2,3-triazol-2-yl]valeramidine as an oily hydrochloride salt.

A stirred mixture of ethyl formate (0.40 ml.), ethyl propionate (0.57 ml.), sodium hydride (0.25 g.) and mineral oil (0.25 g), and EtOH (4 drops) was heated under reflux in ether (15 ml.) for 4 hours. The mixture was filtered and the retained solid was added to a solution of 5-[4-(2-[2,2,2-trifluoroethyl]guanidino)-1,2,3-triazol-2-yl]valeramidine hydrochloride (0.5 g.) in MeOH (5 ml.). The mixture was heated under reflux for 18 hours and then evaporated to dryness. The residue was partitioned between EtOAc and water. The aqueous phase was separated, acidified with HOAc basified with aqueous NaHCO$_3$ and extracted with EtOAc. This extract was dried (MgSO$_4$) and evaporated to dryness. The residue was triturated with EtOAc and filtered to give 0.11 g. of 4-hydroxy-5-methyl-2-(4-[4-(2-[2,2,2-trifluoroethyl]guanidino)-1,2,3-triazol-2yl]butyl)pyrimidine as the acetate salt, m.p. 152°–154°. The filtrate was concentrated to a small volume and treated with a solution of maleic acid (0.06 g.) in a small volume of acetone to give another 0.17 g. of the same product as the hydrogen maleate salt, m.p. 173°–175°.

EXAMPLE 10

A solution of acethydrazide (0.23 g.) and methyl 5-[4-(2-[2,2,3,3-tetrafluoropropyl]guanidino)-1,2,3-triazol-2-yl]valerimidate (1.0 g.) in MeOH (15 ml.) was stirred at room temperature for 5 days. The solution was evaporated to dryness. A solution of the residue in EtOH was heated under reflux for 18 hours and then evaporated to give the crude product. The crude product was purified by medium pressure liquid chromatography on a silica gel column using CH$_2$Cl$_2$/MeOH/aqueous ammonia (s.g. 0.88) 9:1:0.1 v/v/v as eluant to give 0.7 g. of 5-methyl-3-(4-[4-(2-[2,2,3,3-tetrafluoropropyl]guanidino)-1,2,3-triazol-2-yl]butyl)-1,2,4-triazole as an oil. A sample converted to the di(hydrogen maleate) had m.p. 109°–112°.

The starting material may be prepared as follows:

A solution of 5-(4-amino-1,2,3-triazol-2-yl)valeronitrile (2.2 g.) and 2,2,3,3-tetrafluoropropylisothiocyanate (2.3 g.) in acetonitrile (20 ml.) was stirred overnight at room temperature. The mixture was evaporated to dryness, the residue triturated with EtOH and petroleum ether (b.p. 60°–80°) and recrystallised from EtOH to give 2.7 g. of 5-[4-(3-[2,2,3,3-tetrafluoropropyl]thioureido)-1,2,3-triazol-2-yl]valeronitrile, m.p. 99°–101° after recrystallisation from EtOH.

A stirred solution of 5-[4-(3-[2,2,3,3-tetrafluoropropyl]thioureido)-1,2,3-triazol-2-yl]valeronitrile (2.0 g.) in ammoniacal MeOH (6M; 50 ml.) was treated at room temperature with mercuric oxide (2.5 g.). The mixture was stirred at room temperature for 3 days, and then filtered and evaporated to give 2.0 g. of unpurified 5-[4-(2-[2,2,3,3-tetrafluoropropyl]guanidino)-1,2,3-triazol-2-yl]valeronitrile.

A solution of the above nitrile (1.0 g.) in a mixture of CHCl₃ (15 ml.) and MeOH (10 ml.) was saturated at 0° with hydrogen chloride gas. The mixture was maintained at 5° for 2 days in a sealed flask. The mixture was then evaporated to dryness to give the product as a hydrochloride salt. A solution of the hydrochloride salt in CH₂Cl₂ was washed with saturated aqueous NaHCO₃, dried (MgSO₄) and evaporated to give 1.0 g. of methyl 5-[4-(2-[2,2,3,3-tetrafluoropropyl]guanidino)-1,2,3-triazol-2-yl]valerimidate as an oil which as used without further purification.

EXAMPLE 11

A mixture of ethyl formate (22.2 g.), ethyl propionate (15.3 g.), EtOH (1 ml.), a 50% w/w dispersion of NaH in mineral oil (15 g.) and ether (300 ml.) was stirred at room temperature for 18 hours. The mixture was filtered and the residue dissolved in MeOH (150 ml.), and the solution treated with 4-[2-(2-[2,2,2-trifluoroethyl]-guanidino)pyrid-6-ylthio]butanamidine hydrochloride (38 g.). The mixture was stirred with heating under reflux for 5 hours and then evaporated to dryness, and the residue was partitioned between ether and H₂O. The aqueous phase was acidified to pH 1 and washed with ether and then neutralised with saturated aqueous NaHCO₃ solution. The resulting precipitate was collected, dissolved in MeOH and the solution acidified with an ethereal solution of HCl, and the precipitated hydrochloride collected and recrystallised from MeOH to give 4-hydroxy-5-methyl-2-(3-[2-(2-[2,2,2-trifluoroethyl]guanidino)pyrid-6-ylthio]propyl)pyrimidine dihydrochloride, m.p. 244°–246° (decomp.).

The starting material may be obtained as follows:

2-Amino-6-bromopyridine (40 g.) was added to a solution of benzyl mercaptan (83.7 ml.) and sodium (16.4 g.) in EtOH and the mixture stirred and heated under reflux for 72 hours. The mixture was evaporated to dryness and the residue stirred with a mixture of water (1.4 l.) and EtOAc (700 ml.) and acidified to pH 1 with concentrated aqueous hydrochloric acid. The precipitated solid was collected to give 2-amino-6-benzylthiopyridine hydrochloride (30 g.), m.p. 189°–191°.

A solution of 2-amino-6-benzylthiopyridine hydrochloride (47.2 g.) in liquid NH₃ (700 ml.) was stirred while Na (17.0 g.) was added in small portions. When the addition was complete NH₄Cl (21.9 g.) was added and then the mixture was evaporated to dryness. The residue was dissolved in a mixture of EtOH (100 ml.) and H₂O (100 ml.) and the mixture treated with 4-bromobutyronitrile (23 ml.) and stirred at room temperature for 18 hours. The solution was evaporated to dryness and the residue was partitioned between 2N aqueous HCl and ether. The aqueous phase was basified with 10N aqueous NaOH and extracted with EtOAc. The extract was dried over Na₂SO₄ and evaporated to dryness to give 4-(2-aminopyrid-6-ylthio)butyronitrile (36.1 g.) which was used without further purification.

A solution of 4-(2-aminopyrid-6-ylthio)butyronitrile (36 g.) and 2,2,2-trifluoroethylisothiocyanate (22 ml.) in acetonitrile (100 ml.) was left at room temperature for 18 hours. The crystalline precipitate was collected and washed with cold EtOH to give 4-[2-(3-[2,2,2-trifluoroethyl]thioureidopyrid-6-ylthio]butyronitrile, m.p. 131°–133°.

A mixture of 4-[2-(3-[2,2,2-trifluoroethyl]thioureido)-pyrid-6-ylthio]butyronitrile (29 g.), yellow mercuric oxide (29 g.) and a saturated solution of ammonia in EtOH (100 ml.) was stirred at room temperature for 24 hours and then filtered. The filtrate was evaporated to dryness and the residue triturated with petroleum ether (b.p. 60°–80°) and collected to give 4-[2-(2-[2,2,2-trifluoroethyl]guanidino)pyrid-6-ylthio]butyronitrile (24 g.), m.p. 89°–91°.

A solution of 4-[2-(2-[2,2,2-trifluoroethyl]guanidino)-pyrid-6-ylthio]butyronitrile (36.5 g.) in CHCl₃ (150 ml.) and MeOH (150 ml.) was saturated with HCl gas at 0° and then kept at 0° for 72 hours. The mixture was evaporated to dryness, and the residue partitioned between aqueous K₂CO₃ and CHCl₃. The aqueous phase was extracted a further twice with CHCl₃ and the combined CHCl₃ extracts dried and evaporated to dryness. A solution of the residue in MeOH (200 ml.) was treated with NH₄Cl (8.6 g.) and the mixture stirred at room temperature for 2 hours and then evaporated to dryness. The residue was triturated with acetonitrile and the insoluble material collected to give 4-[2-(2-[2,2,2-trifluoroethyl]guanidino)pyrid-6ylthio]butanamidine hydrochloride (38 g.) which was used without further purification. A sample characterised as the dihydrochloride had m.p. 118°–120°.

EXAMPLE 12

A mixture of ethyl formate (0.37 g.), ethyl propionate (0.6 g.) and sodium hydride (50% w/v dispersion in mineral oil; 0.5 g.) was heated under reflux in ether (15 ml.) containing EtOH (1 drop). After 2 hours the white precipitate was filtered off under dry conditions and heated under reflux with 5-[4-(2-[2,2,2-trifluoroethyl]-guanidino)pyrimid-2-yl]valeramidine hydrochloride (0.75 g.) in MeOH (10 ml.) for 24 hours. The mixture was then evaporated to dryness and the residue partitioned between dilute aqueous HOAc (20 ml.) and EtOAc (10 ml.). The aqueous layer was separated and the pH adjusted to approximately 7 with aqueous sodium bicarbonate. The aqueous mixture was then extracted with EtOAc (2×20 ml.), the EtOAc layers were combined and evaporated to dryness and the residue was purified by preparative thin layer chromatography using a mixture of chloroform/MeOH aqueous ammonia (s.g. 0.88) 8:2:0.1 v/v/v as eluant. The appropriate material isolated from the plates gave on trituration with acetonitrile 0.1 g. of 4-hydroxy-5-methyl-2-[4-(4-[2-(2,2,2-trifluoroethyl)guanidino]pyrimid-2-yl)butyl]pyrimidine, m.p. 210°–212°.

The starting material may be prepared as follows:

Ethyl 5-cyanovalerimidate (75 g.) was stirred for 18 hous in MeOH (200 ml.) containing ammonium chloride (26.4 g.). The mixture was then filtered and the filtrate evaporated to dryness. The residue was heated under reflux in EtOH (250 ml.) containing triethylamine (285 ml.) and 2-chloroacrylonitrile (106 g.). After 2 hours the mixture was cooled, added to water (1 l.) and the pH adjusted to 4 with HOAc. The aqueous mixture was then treated with charcoal, filtered and the filtrate extracted with EtOAc (300 ml.). The aqueous layer was separated and the pH adjusted to 9 with aqueous sodium hydroxide. The aqueous mixture was then extracted with EtOAc (2×500 ml.). The combined extracts were evaporated to dryness and the residue was recrystallised from acetonitrile to give 16 g. of 5-(4-aminopyrimid-2-yl)valeronitrile.

A mixture of 5-(4-aminopyrimid-2-yl)valeronitrile (30 g.) and 2,2,2-trifluoroethylisothiocyanate (30 g.) in acetonitrile (50 ml.) was heated under reflux for 18 hours. The mixture was then evaporated to dryness and the residue dissolved saturated methanolic ammonia. The resulting solution was stirred and mercuric oxide (48 g.) added. After 2 hours the mixture was filtered through diatomaceous earth and the filtrate evaporated to dryness. The residue was triturated with ether and the solid product filtered off to give 39 g. of 5-[4-(2-[2,2,2-trifluoroethyl]guanidino)pyrimid-2-yl]valeronitrile.

A solution of 5-[4-(2-[2,2,2-trifluoroethyl]guanidino)pyrimid-2-yl]valeronitrile (39 g.) in a mixture of CHCl$_3$ (250 ml.) and MeOH (150 ml.) was cooled to −10° and saturated with hydrogen chloride gas. The mixture was then allowed to stand at 0° for 60 hours. The mixture was then evaporated to dryness and a mixture of potassium carbonate (100 g.) in water (300 ml.), cooled to 5° was added. The resulting mixture was extracted with CHCl$_3$ (2×200 ml.) and the combined organic extracts dried (MgSO$_4$) and evaporated to dryness. The residue was stirred in MeOH (150 ml.) with ammonium chloride (7 g.). After 3 hours the mixture was filtered and ether (500 ml.) was added. The precipitated solid was filtered off to give 30 g. of 5-[4-(2-[2,2,2-trifluoroethyl]guanidino)pyrimid-2-yl]valeramidine hydrochloride which was used without further purification.

EXAMPLE 13

To 4-[4-(2-[2,2,2-trifluoroethyl]guanidino)pyrimid-2-ylthio]butyronitrile (3.0 g.) in chloroform (40 ml.) and MeOH (20 ml.) at 0° was added excess hydrogen chloride gas. The resulting mixture was allowed to stand at room temperature for 2 days and then evaporated to dryness. The residue was extracted from potassium carbonate (10 g.) in water (50 ml.) with chloroform (3×50 ml.). The organic layer was evaporated to dryness and the crude imino-ether used without further purification. A portion (1.6 g.) of this material was dissolved in MeOH (5 ml.) and cyanamide (0.2 g.) added. The solution was stirred at room temperature for 1 hour and the white precipitate was then filtered off to give 1.1 g. of N-cyano-4-[4-(2-[2,2,2-trifloroethyl]guanidino)pyrimid-2-ylthio]butanamidine, m.p. 224° (yield 66%).

EXAMPLE 14

To a solution of N-cyano-4-[4-(2-[2,2,2trifluoroethyl]guanidino)pyrimid-2-ylthio]butanamidine (0.6 g.) in a mixture of chloroform (10 ml.) and MeOH (5 ml.) was added water (0.04 g.). The solution was cooled to 5° and saturated with hydrogen chloride gas. After 2 hours at 5° the mixture was evaporated to dryness, the residue dissolved in water and aqueous ammonia added until the mixture was strongly basic. The precipitated solid was filtered off to give 0.2 g. of N-carbamoyl-4-[4-(2-[2,2,2-trifluoroethyl]guanidino)pyrimid-2-ylthio]butanamidine, m.p. 112°–115° (yield 31%).

EXAMPLE 15

A solution of methyl 4-[4-(2-[2,2,2-trifluoroethyl]guanidino)pyrimid-2-ylthio]butyrimidate (0.5 g.) and 2,2,2-trifluoroethylamine hydrochloride (0.2 g.) in MeOH (3 ml.) was kept at 20° for 2 hours. The solvent was evaporated in vacuo and the resulting gum was purified by preparative thin layer chromatography on silica plates eluted with EtOAc/MeOH/aqueous ammonium (s.g. 0.880) 6:1:1 v/v/v. The product was dissolved in acetone and additin of maleic acid gave N-(2,2,2-trifluoroethyl)-4-[4-(2-[2,2,2-trifluoroethyl]guanidino)pyrimid-2-ylthio]butyramidine mono maleate mono hydrate, m.p. 138°–140°.

EXAMPLE 16

A solution of methyl 4-[4-(2-[2,2,2-trifluoroethyl]guanidino)pyrimid-2-ylthio]butyrimidate (0.6 g.) and 1,2-diaminoethane (0.1 g.) in MeOH (8 ml.) was kept at room temperature for 16 hours, and then evaporated to dryness. The residue was purified by medium pressure liquid chromatography using a mixture of chloroform/MeOH/ aqueous ammonia (s.g. 0.880) 9:1:0.05, v/v/v as eluant. The appropriate fractions were evaporated and the residue recrystallised from acetonitrile to give 0.2 g. of 2-[3-(4-[2-(2,2,2-trifluoroethyl)guanidino]pyrimid-2-ylthio)propyl]-1-imidazoline, m.p. 184°–186° (Yield 32%).

EXAMPLE 17

A solution of methyl 5-[4-(2-[2,2,2-trifluoroethyl]guanidino)pyrimid-2-yl]valerimidate (0.5 g.) and methanesulphonamide (0.4 g.) in MeOH (4 ml.) was allowed to stand for two days and then evaporated to dryness. The residue was purified by preparative thin layer chromatography using a mixture of chloroform/MeOH/aqueous ammonia (s.g. 0.880) 8:2:0.1 v/v/v as eluant. The appropriate band was isolated and treated with maleic acid in acetone/ether mixture to give 0.14 g. of N-methanesulphonyl-5-[4-(2-[2,2,2-trifluoroethyl]guanidino)pyrimid-2-yl]valeramidine hydrogen maleate, m.p. 136°–138° (yield 15%).

EXAMPLE 18

A solution of methyl 5-[4-(2-[2,2,2-trifluoroethyl]guanidino)pyrimido-2-yl]valerimidate (0.5 g.) in MeOH (6 ml.) was treated with ethyl carbazate (0.28 g.) and the solution allowed to stand for 18 hours. The mixture was evaporated to dryness and the residue triturated with ether/EtOH to give N-ethoxycarbonyl-5-[4-(2-[2,2,2-trifluoroethyl]guanidino)pyrimid-2-yl]valeramidrazone (0.39 g.), m.p. 137°–139° (65%).

EXAMPLE 19

A solution of methyl 5-[4-(2-[2,2,2-trifluoroethyl]guanidino)pyrimid-2-yl]valerimidate (0.55 g.) and 2-amino-4-methylimidazole acetate (0.26 g.) in MeOH (5 ml.) was allowed to stand for 4 days. The mixture was then evaporated to dryness and the residue purified by medium pressure liquid chromatography using a mixture of chloroform/MeOH/aqueous ammonia (s.g. 0.880) 9:1:0.05 v/v/v as eluant. The appropriate fraction was treated with excess maleic acid in acetone to give 0.18 g. of N-(4-methylimidazol-2-yl)-5-[4-(2-[2,2,2-trifluoroethyl)guanidino)pyrimid-2-yl]valeramidine dihydrogen maleate, m.p. 184°–187°.

EXAMPLE 20

A solution of methyl N-cyano-5-(4-[2-(2,2,2-trifluoroethyl)guanidino]pyrimid-2-yl)valerimidate (0.12 g.) and 33% w/v ethanolic methylamine (15 ml.) in MeOH (3 ml.) was allowed to stand for 24 hours. The solvent was removed and the residue was purified by chromatography on silica to give a gummy solid. The solid was converted in acetone to the maleate salt which was filtered and washed with acetone to give N'-methyl-N''-cyano-5-(4-[2-(2,2,2-trifluoroethyl)guanidino]pyrimid-2-yl)valeramidine dihydrogen maleate (0.027 g.), m.p. 190°–192°.

The starting material may be prepared as follows:

To a solution of methyl 5-[4-(2-[2,2,2-trifluoroethyl]guanidino)pyrimid-2-yl]valerimidate dihydrochloride (0.5 g.) in MeOH (10 ml.) was added triethylamine (0.125 g.) and cyanamide (0.08 g.) and the mixture was stirred for 18 hours at 20°. Volatile material was evaporated in vacuo and the residue was triturated with a mixture of ether and EtOH to give crude methyl N-cyano-5-[4-(2-[2,2,2-trifluoroethyl]guanidino)pyrimid-2-yl]valerimidate as a white solid which was used without further purification.

EXAMPLE 21

A mixture of 6-[4-(2-[2,2,2-trifluoroethyl]guanidino)-pyrimid-2-yl]hexanamidine hydrochloride (0.37 g.), 2-chloroacrylonitrile (0.17 g.) and triethylamine (0.4 g.) was heated under reflux in EtOH (5 ml.) for 6 hours. The mixture was then evaporated to dryness and the residue partitioned between dilute aqueous sodium hydroxide and EtOAc. The EtOAc layer was evaporated to dryness and the residue triturated with acetonitrile to give 0.2 g. of 4-amino-2-[5-(4-[2-(2,2,2-trifluoroethyl)-guanidino]pyrimid-2-yl)pentyl]pyrimidine, m.p. 114°-117°.

The starting material may be prepared in a similar manner to that described in Example 12, parts 2 to 4, using ethyl 6-cyanohexanimidate in place of ethyl 5-cyanovalerimidate.

EXAMPLE 22

N-Ethoxycarbonyl-5-[4-(2-[2,2,2-trifluoroethyl]-guanidino)pyrimid-2-yl]valeramidrazone (0.21 g.) was heated at 150° for 10 minutes. The resulting glass was crystallised from acetone to give 3-hydroxy-5-(4-[4-(2-[2,2,2-trifluoroethyl]guanidino)pyrimid-2-yl]butyl)-1,2,4-triazole as a white solid (0.118 g.), m.p. 209°-210°.

EXAMPLE 23

To ethyl 2-acetylpropionate (0.4 g.) in MeOH (5 ml.) was added sodium hydride (a 50% w/w dispersion in oil; 0.16 g.). To the resulting solution was added 3-(2-[4-(2-[2,2,2-trifluoroethyl]guanidino)pyrimid-2-yl]ethoxy)-propanamidine hydrochloride (0.6 g.). The mixture was heated under reflux for 6 hours and then evaporated to dryness. The residue was partitioned between aqueous sodium bicarbonate and EtOAc. The EtOAc layer was evaporated to dryness and the residue treated with maleic acid in acetone to give 4-hydroxy-5,6-dimethyl-2-(2-[2-(4-[2-(2,2,2-trifluoroethyl)guanidine]pyrimid-2-yl)ethoxy]ethyl)pyrimidine hydrogen maleate (0.14 g.), m.p. 150°-153°.

The 3-(2-[4-(2-[2,2,2-trifluoroethyl]guanidino)pyrimid-2-yl]ethoxy)propanamidine hydrochloride used as starting material may be prepared as follows:

To a mixture of bis-(2-cyanoethyl)ether (62 g.) and EtOH (23 g.) in ether (300 ml.) at 0° was added hydrogen chloride gas (18 g.). The mixture was allowed to stand at 0° for 3 days and then the lower layer was separated. This mixture was added to a solution of potassium carbonate (140 g.) in water (400 ml.) at −10° and the mixture was extracted with chloroform (200 ml.). The chloroform extract was evaporated to dryness to give an oily residue, of which 35 g. was stirred for 18 hours in EtOH (100 ml.) with ammonium chloride (12 g.). The mixture was filtered and the filtrate evaporated to dryness. The residue was heated under reflux in EtOH (150 ml.) with 2-chloroacrylonitrile (16.5 ml.) and triethylamine (55 ml.) for 2 hours. The mixture was then evaporated to dryness and the residue partitioned between aqueous HOAc and EtOAc. The aqueous layer was separated and basified with dilute sodium hydroxide and extracted with EtOAc three times. The combined extracts were evaporated to dryness. The residue was purified by medium pressure liquid chromatography using chloroform/MeOH/aqueous ammonia (s.g. 0.880) 15:1:0.05, v/v/v as eluant. This gave 4.7 g. of 3-(2-[4-aminopyrimid-2-yl]ethoxy)propionitrile. The n.m.r. spectrum in d$_6$DMSO included the following resonances: 2.7 (t, 2H), 2.8 (t, 2H), 3.5 (t, 2H); 3.8 (t, 2H); 6.2 (d, 1H); 6.6 (br s, 2H), 7.9 (d, 1H).

This material (4.5 g.) was heated under reflux in acetonitrile (5 ml.) with 2,2,2-trifluoroethylisothiocyanate (5 g.) for 2 hours. The mixture was then evaporated to dryness and the residue dissolved in saturated ethanolic ammonia (100 ml.). Mercuric oxide (9 g.) was then added to the stirred solution. After 30 minutes the mixture was filtered and the filtrate evaporated to dryness to give 3-(2-[4-(2-[2,2,2-trifluoroethyl]guanidino)pyrimid-2-yl]ethoxy)propionitrile (3.5 g.). The n.m.r. spectrum of this material in d$_6$DMSO included the following resonances: 2.7 (t, 2H); 2.9 (t, 2H); 3.6 (t, 2H); 3.8 (t, 2H); 4.15 (q, 2H), 6.5 (d, 1H), 7.3 (br s, 1H), 7.9 (br s, 2H); 8.15 (d, 1H).

This material (3.5 g.) was dissolved in a mixture of MeOH (30 ml.) and chloroform (30 ml.) and the mixture saturated with hydrogen chloride at −10°. The solution was then allowed to stand at 0° for 2 days and then evaporated to dryness. The residue was added to a solution of potassium carbonate (30 g.) in water (70 ml.) and this mixture was then extracted with chloroform (50 ml.). The organic layer was evaporated to dryness. The residue (1 g.) was stirred in MeOH (4 ml.) with ammonium chloride (0.16 g.) for 6 hours. The mixture was then evaporated to dryness to give 3-(2-[4-(2-[2,2,2-trifluoroethyl]guanidino)-pyrimid-2-yl]ethoxy)-propanamidine hydrochloride, which was used without further purification.

EXAMPLE 24

5-(4-[2-(2,2,2-Trifluoroethyl)guanidino]pyrimid-2-yloxy)valeramidine hydrochloride (0.5 g.) was added to a solution of ethyl acetoacetate (0.352 g.) and sodium hydride (0.07 g.) in MeOH (6 ml.). The resulting solution was heated under reflux for 18 hours. The solvent was evaporated and the residue taken up in aqueous HOAc and extracted with EtOAc. The aqueous layer was basified with potassium carbonate and extracted with EtOAc. Work up gave a sticky solid which was crystallised from acetonitrile to give 4-hydroxy-6-methyl-2-[4-(4-[2-(2,2,2-trifluoroethyl)guanidino]pyrimid-2-yloxy)butyl]pyrimidine as white crystals (0.22 g.), m.p. 191°-193°.

The starting material may be prepared as follows:

4-Cyanobutanol (10 g.) was added to sodium hydride (2.75 g.) in t-butanol (95 ml.) and the solution warmed to 40°. 4-[2-(2,2,2-Trifluoroethyl)guanidino]-2-methyl-sulphinylpyrimidine (European patent publication No. 30092) was added over 10 minutes and the solution kept at 40° for 2 hours then at room temperature for 18 hours. The solvent was removed under vacuum and the residue washed with water, then ether, to give 5-[4-(2-[2,2,2-trifluoroethyl]guanidino)pyrimid-2-yloxy]-valeronitrile (8.5 g.), m.p. 134°-136°.

The above nitrile (3 g.) was dissolved in dry chloroform (40 ml.) and MeOH (20 ml.), cooled to 0° and saturated with hydrogen chloride gas. The mixture was kept at 0° for 60 hours then volatile material was evaporated in vacuo. The residue was shaken with cold aqueous potassium carbonate solution (50 ml.) and extracted with chloroform (3×50 ml.). The combined extracts were dried (MgSO$_4$) and evaporated in vacuo to give methyl 5-[4-(2-[2,2,2-trifluoroethyl]guanidino)pyrimid-2-yloxy]valerimidate as a gum which was used without further purification.

Methyl 5-(4-[2-(2,2,2-trifluoroethyl)guanidino]pyrimid-2-yloxy)valerimidate (1.5 g.) in MeOH (15 ml.) was treated with ammonium chloride (0.25 g.) and the solution stirred at room temperature for 2 hours. Ether was added until the solution became cloudy. Continued stirring caused precipitation of a solid which was filtered to give 5-(4-[2-(2,2,2-trifluoroethyl)guanidino]-pyrimid-2-yloxy)valeramidine hydrochloride, (1.52 g.), m.p. 156°–158°.

EXAMPLE 25

To a solution of sodium hydride (50% w/w dispersion in mineral oil; 0.04 g.) in t-butanol (5 ml.) was added 3-methyl-5-(3-hydroxypropylthio)-1,2,4-triazole (0.17 g.) and 2-methylsulphinyl-4-(2-[2,2,2-trifluoroethyl]guanidino)pyrimidine (0.14 g.) (European patent publication No. 30092). The mixture was heated under reflux for 3 hours and evaporated to dryness. The residue was partitioned between EtOAc and 2N aqueous hydrochloric acid. The acid extract was basified with 2N aqueous sodium hydroxide and extracted with EtOAc. This extract was dried (MgSO$_4$) and evaporated to dryness. The residual gum was purified by preparative thin layer chromatography using EtOAc/MeOH/aqueous ammonia (s.g. 0.880) 6:1:1 v/v/v as eluant. Material isolated from the appropriate band was dissolved in EtOAc, filtered and the filtrate treated with a solution of maleic acid (0.1 g.) in EtOAc to give 3-methyl-5-(3-[4-(2-[2,2,2-trifluoroethyl]guanidino)-pyrimid-2-yloxy]propylthio)-1,2,4-triazole hydrogen maleate hemihydrate (0.05 g.), m.p. 157°–161° (decomp.).

The starting material may be prepared as follows:

To a solution of sodium hydroxide (0.4 g.) in water (5 ml.) was added 3-chloropropan-1-ol (0.83 ml.) and 3-methyl-5-mercapto-1,2,4-triazole (1.1 g.) and the mixture was heated at 100° for 1.5 hours. The solvent was evaporated and the residue was extracted twice with EtOAc/EtOH 50:50 v/v (20 ml.). The extracts were combined and evaporated to dryness. The residual solid was recrystallised from EtOAc to give 3-methyl-5-(3-hydroxypropylthio)-1,2,4-triazole (0.4 g.) which was used without further purification.

EXAMPLE 26

Dry hydrogen chloride gas was bubbled into a solution of 1-[2-(2-cyanoethoxy)ethyl]-3-[2-(2,2,2-trifluoroethyl)guanidino]pyrazole (330 mg.) in MeOH (15 ml.) and chloroform (15 ml.) at 0° till saturated. The mixture was kept at 0° for 24 hours. The solvent was evaporated in vacuo and the residue basified with ice-cold 10% w/v aqueous potassium carbonate solution (10 ml.). The mixture was extracted with chloroform (3×10 ml.), the extracts dried (MgSO$_4$) and evaporated in vacuo to give a pale yellow oil (330 mg.). This oil was dissolved in MeOH (10 ml.), cyanamide (100 mg.) added, and the mixture stirred at room temperature for 17 hours. The solution was evaporated to dryness and the residue was purified by preparative thin layer chromatography, using a mixture of triethylamine/EtOH/EtOAc 1:9:9 v/v/v as eluant, to give N-cyano-3-[2-(3-[2-(2,2,2-trifluoroethyl)guanidino]pyrazol-1-yl)ethoxy]propionamidine (0.21 g.) having the following n.m.r. spectrum in d$_6$DMSO: 7.4 (d, 1H); 5.6 (d, 1H); 4.0 (br m, 4H); 3.65 (br m, 4H); 2.5 (m, 2H).

The starting material may be prepared as follows:

2-Hydroxyethylhydrazine (7.6 g.) was added slowly to a solution of potassium carbonate (13.8 g.) in water (40 ml.). The mixture was cooled to 0°, then 2-chloroacrylonitrile (8.75 g.) was added slowly with vigorous stirring. Stirring was continued for a further 17 hours and the mixture was then continuously extracted with EtOAc for 20 hours. On evaporation of the solvent, 3-amino-1-(2-hydroxyethyl)pyrazole was obtained (7.7 g.; 60%), b.p. 170/0.5 mm.

A mixture of 2,2,2-trifluoroethylisothiocyanate (13.8 g.) and 3-amino-1-(2-hydroxyethyl)pyrazole (12.5 g.) in acetonitrile dried over 4A molecular sieve (30 ml.) was stirred at room temperature for 4 hours. A precipitate formed after 30 minutes. Filtration gave 1-(2-hydroxyethyl)-3-[3-(2,2,2-trifluoroethyl)thioureido]pyrazole (12.1 g.; 46%), m.p. 145°–146°.

To a solution of 1-(2-hydroxyethyl)-3-[3-(2,2,2-trifluoroethyl)thioureido]pyrazole (20.0 g.) in 5N ammonia in EtOH solution (700 ml.) was added yellow mercuric oxide (64.8 g.) with stirring. Stirring was continued for a period of 2 hours. The mixture was filtered through diatomaceous earth and the solvent then evaporated to dryness in vacuo. The residual oil was triturated with ether to give 1-(2-hydroxyethyl)-3-[2-(2,2,2-trifluoroethyl)guanidino]pyrazole (18.5 g.; 99%), m.p. 82°.

Acrylonitrile (0.8 g.) was added to a solution of 1-(2-hydroxyethyl)-3-[2-(2,2,2-trifluoroethyl)guanidino]-pyrazole (2.51 g.) in acetonitrile (10 ml.). Benzyltrimethylammonium hydroxide (40% w/v aqueous solution; 10 μl) was added. After stirring at room temperature for 1 hour, the solution was evaporated to dryness in vacuo, and the residue purified by medium pressure chromatography using triethylamine/EtOH/EtOAc 1:1:9 v/v/v as eluant to give 1-[2-(2-cyanoethoxy)ethyl]-3-[2-(2,2,2-trifluoroethyl)guanidino]pyrazole (1.0 g.) having the following n.m.r. spectrum in d$_6$DMSO: 7.6 (d, 1H); 5.8 (d, 1H); 4.2 (m, 2H); 4.1 (t, 2H); 3.8 (t, 2H); 3.6 (t, 2H); 2.7 (t, 2H).

EXAMPLE 27

A mixture of methyl 5-[5-(2-[2,2,2-trifluoroethyl]guanidino)tetrazol-2-yl]valerimidate (0.6 g.), acethydrazide (0.2 g.) and MeOH (20 ml.) was stirred at room temperature for 2 hours. The mixture was evaporated. The residue was triturated with ether containing a trace of EtOH and filtered to give 0.5 g. of N-acetylamino-5-[5-(2-[2,2,2-trifluoroethyl]guanidino)tetrazol-2-yl]valeramidine. A sample that had been triturated with EtOH and filtered had an m.p. 159°–161° (decomp.).

The starting material may be prepared as follows:

A stirred mixture of 5-aminotetrazole (8.5 g.), NaOH (4.0 g.), and water (40 ml.) was treated at room temperature with a solution of 5-bromovaleronitrile (16.2 g.) in acetone (160 ml.). The mixture was heated under reflux for 4 hours. The solvent was evaporated and the residue was partitioned between water and EtOAc. The organic phase was separated, dried (MgSO$_4$) and evaporated to give an oily solid. The oily solid was triturated with ether and filtered. The filtrate was evaporated to give 11.5 g. of an oil which was purified by column chromatography on silica gel using EtOAc as eluant to give 2.7 g. of partially purified 5-(5-aminotetrazol-2-yl)valeronitrile, m.p. 59°–61°.

5-(5-Aminotetrazol-2-yl)valeronitrile (1.0 g.) was melted and treated with 2,2,2-trifluoroethylisothiocyanate (1.0 ml.). The mixture was kept at room temperature overnight to give a white solid. The white solid was triturated with petroleum ether (b.p. 40°–60°) and filtered to give 1.5 g. of partially purified 5-[5-(3-[2,2,2-trifluoroethyl]thioureido)tetrazol-2-yl]valeronitrile, m.p. 94°–96°.

A mixture of partially purified 5-[5-(3-[2,2,2-trifluoroethyl]thioureido)tetrazol-2-yl]valeronitrile (1.5 g.), mercuric oxide (1.5 g.) and ethanolic ammonia (6M; 20 ml.) was stirred at room temperature overnight. The mixture was filtered and evaporated. The residue was recrystallised from EtOH to give 1.1 g. of 5-[5-(2-[2,2,2-trifluoroethyl]guanidino)tetrazol-2-yl]valeronitrile, m.p. 140°–141°.

A mixture of 5-[5-(2-[2,2,2-trifluoroethyl]guanidino)tetrazol-2-yl]valeronitrile (0.5 g.), CHCl$_3$ (15 ml.) and MeOH (10 ml.) was saturated at 0° with HCl gas. The mixture was kept at 5° for 48 hours. The mixture was evaporated to dryness and partitioned between EtOAc and saturated aqueous NaHCO$_3$. The organic layer was separated, dried (MgSO$_4$) and evaporated to give 0.6 g. of methyl 5-[5-(2-[2,2,2-trifluoroethyl]guanidino)tetrazol-2-yl]valerimidate which was used without further purification.

EXAMPLE 28

A mixture of N-acetylamino-5-[5-(2-[2,2,2-trifluoroethyl]guanidino)tetrazol-2-yl]valeramidine (0.3 g.) and EtOH (10 ml.) was heated overnight by an oil bath maintained at 70°. The oil bath temperature was raised to 90° and the mixture was heated for another 48 hours. The mixture was evaporated to dryness. A solution of the residue in MeOH was treated with maleic acid (0.191 g.) and re-evaporated. The residue was recrystallised from EtOH to give 0.21 g. of 3-methyl-5-(4-[5-(2-[2,2,2-trifluoroethyl]guanidino)tetrazol-2-yl]butyl)-1,2,4-triazole 2.25 maleate, m.p. 131°–133°.

EXAMPLE 29

A solution of 5-(3-[2-(2,2,2-trifluoroethyl)guanidino]-1,2,4-triazol-1-yl)valeramidine hydrochloride (1 g.) in MeOH (14 ml.) was treated with the sodium salt of ethyl 2-formylpropionate (1.95 g.) and the suspension heated under reflux for 3.5 hours. This suspension was evaporated and the residue partitioned between water and ether. The aqueous layer was acidified with glacial HOAc to pH 3 and further extracted with ether. Neutralisation with aqueous ammonia (s.g. 0.880) and extraction with EtOAc gave a white solid which was crystallised twice from acetonitrile to give 4-hydroxy-5-methyl-2-[4-(3-[2-(2,2,2-trifluoroethyl)guanidino]-1,2,4-triazol-1-yl)butyl]pyrimidine (0.127 g.; 12%), m.p. 235°–237°.

The starting material may be prepared as follows:

3-Amino-1,2,4-triazole (4.2 g.) was added to a solution of sodium methoxide in MeOH (1.2 g. sodium in 30 ml. MeOH) and the solution stirred for 0.5 hours at room temperature. 5-Bromovaleronitrile (8.1 g.) was added and the solution heated under reflux for 21 hours. The solution was evaporated and the residue partitioned between water and EtOAc. The extracts were washed with brine, dried over MgSO$_4$ and evaporated to give a pale yellow oil (6.5 g.) which was purified by medium pressure liquid chromatography using EtOAc/MeOH 6:1 v/v as eluant. The colourless oil obtained was used without characterisation for the following reaction.

The crude 1-(4-cyanobutyl)-3-amino-1,2,4-triazole (5.45 g.) in acetonitrile (80 ml.) was treated with 2,2,2-trifluoroethylisothiocyanate (4.4 g.) and the solution heated under reflux for 3.5 hours. Evaporation gave a white sticky solid which was triturated with ether/EtOH to give 5-(3-[3-(2,2,2-trifluoroethyl)thioureido]-1,2,4-triazol-1-yl)valeronitrile (4.04 g.) as a white solid, m.p. 136°–138°.

This nitrile (3.6 g.) in MeOH (80 ml.) and acetonitrile (5 ml. ) was treated with mercuric oxide (3.06 g.) and methanolic ammonia (15 ml.). After stirring for 1.5 hours the black suspension was filtered through diatomaceous earth and the filtrates evaporated to give a white solid. The solid was washed with ether and filtered to give 5-[3-(2-[2,2,2-trifluoroethyl]guanidino)-1,2,4-triazol-1-yl]valeronitrile (2.87 g.) as a white solid, m.p. 200°–201° after recrystallisation from EtOH.

A solution of 5-[3-(2-[2,2,2-trifluoroethyl]guanidino)-1,2,4-triazol-1-yl]valeronitrile (2 g.) in MeOH (15 ml.) and chloroform (35 ml.) at 0° was saturated with HCl gas and the solution allowed to stand for 62 hours at 0°. The solvent was evaporated and the residue partitioned between aqueous potassium carbonate and chloroform. The chloroform extracts were washed, dried and evaporated to give methyl 5-[3-(2-[2,2,2-trifluoroethyl]guanidino)-1,2,4-triazol-1-yl]valerimidate as pale yellow oil.

A solution of methyl 5-[3-(2-[2,2,2-trifluoroethyl]guanidino)-1,2,4-triazol-1-yl]valerimidate (1 g.) in MeOH (12 ml.) and ammonium chloride (0.162 g.) was stirred for 3 hours at room temperature. The solvent was removed to give 5-[3-(2-[2,2,2-trifluoroethyl]guanidino)-1,2,4-triazol-1-yl]valeramidine hydrochloride as a yellow gum, which was used without further purification.

EXAMPLE 30

A solution of methyl 5-[3-(2-[2,2,2-trifluoroethyl]guanidino)-1,2,4-triazol-1-yl]valerimidate (0.5 g.) in MeOH (5 ml.) and acethydrazide (0.17 g.) was allowed to stand at room temperature for 3 hours. The solution was evaporated to give a sticky solid which was triturated with ether/EtOH to give N-acetylamino-5-[3-(2-[2,2,2-trifluoroethyl]guanidino)-1,2,4-triazol-1-yl]valeramidine as a white solid (0.71 g.), m.p. 157°–159°.

EXAMPLE 31

N-Acetylamino-5-[3-(2-[2,2,2-trifluoroethyl]guanidino)-1,2,4-triazol-1-yl]valeramidine (0.55 g.) was heated at 170° for 12 minutes. The resulting glass was boiled with acetone and the solid obtained crystallised from acetonitrile to give 3-methyl-5-(4-[3-(2-[2,2,2-trifluoroethyl]guanidino)-1,2,4-triazol-1-yl]butyl)-1,2,4-triazole as a white solid (0.34 g., 65%), m.p. 175°–176°.

EXAMPLE 32

A mixture of methyl 4-[2-(2-[2,2,2-trifluoroethyl]guanidino)pyrid-6-yloxy]butyrimidate (0.3 g.), ammonium chloride (0.054 g.) and MeOH (5 ml.) was stirred at room temperature for 1 hour. The mixture was treated with the sodium salt of ethyl 2-formylpropionate [prepared from ethylformate (0.37 g.), ethyl propionate (0.51 g.) and a 50% w/w dispersion of sodium hydride in oil (0.5 g.) as in the first part of Example 11] and heated under reflux for 18 hours and then evaporated to dryness. The residue was partitioned between ether and H₂O and the aqueous phase acidified to pH 1 and washed with ether. The aqueous phase was neutralised with NaHCO₃ and extracted three times with EtOAc, and the combined EtOAc extracts dried and evaporated to dryness. A solution of the residue in acetone was added to a solution of maleic acid in acetone and the precipitate collected and crystallised from aqueous EtOH to give 4-hydroxy-5-methyl-2-(3-[2-(2-[2,2,2-trifluoroethyl]guanidino)pyrid-6-yloxy]propyl)pyrimidine hydrogen maleate (0.1 g.), m.p. 209°–210°.

The imidate used as starting material may be prepared as follows:

A mixture of 4-hydroxybutyronitrile (0.85 g.), a 50% w/w dispersion of sodium hydride in mineral oil (0.48 g.) and sulpholane (5 ml.) was stirred at room temperature for 1 hour. The mixture was treated with 2-amino-6-bromopyridine (0.87 g.) and the mixture heated with stirring at 130° for 18 hours. The cooled mixture was diluted with water (20 ml.), acidified with concentrated aqueous HCl and washed with ether. The aqueous phase was basified with 10N aqueous NaOH, extracted three times with EtOAC, and the combined extracts dried and evaporated to dryness.

A solution of the residue in acetonitrile (5 ml.) was treated with 2,2,2-trifluoroethylisothiocyanate, and the solution heated under reflux for 1 hour and then evaporated to dryness. The residue was stirred with 2N aqueous HCl (20 ml.) and ether (20 ml.) and the insoluble material collected.

The solid was dissolved in methanolic ammonia solution, and the solution treated with yellow mercuric oxide (2 g.) and then stirred at room temperature for 18 hours. The mixture was filtered and the filtrate evaporated to dryness to give 4-[6-(2-[2,2,2-trifluoroethyl]-guanidino)pyrid-2-yloxy]butyronitrile (1.0 g.).

A solution of 4-[2-(2-[2,2,2-trifluoroethyl]guanidino)-pyrid-6-yloxy]butyronitrile in a mixture of CHCl₃ (10 ml.) and MeOH (5 ml.) was saturated with HCl gas at 0° and then kept at 0° for 3 days. The solution was evaporated to dryness and the residue shaken with a mixture of CHCl₃ and aqueous K₂CO₃. The CHCl₃ phase was dried and evaporated to dryness to give methyl 4-[2-(2-[2,2,2-trifluoroethyl]guanidino)pyrid-6-yloxy]butyrimidate (0.8 g.) which was used without further purification.

EXAMPLE 33

A solution of methyl 4-[2-(2-[2,2,2-trifluoroethyl]-guanidino)pyrid-6-ylthio]butyrimidate (0.2 g.) and sulphamide (0.2 g.) in MeOH was left at room temperature for 24 hours and then evaporated to dryness. The residue was partitioned between H₂O and EtOAc and the EtOAc phase dried and evaporated to dryness. A solution of the residue in acetone was added to a solution of maleic acid in acetone and the precipitate collected and crystallised from aqueous EtOH to give N-sulphamoyl-4-[2-(2-[2,2,2-trifluoroethyl]guanidino)pyrid-6-ylthio]-butyramidine hydrogen maleate, m.p. 176°–177°.

EXAMPLE 34

A solution of methyl 5-[2-(2-[2,2,2-trifluoroethyl]-guanidino)pyrid-6-ylthio]valerimidate (0.3 g.) and N-methyl-2,2-diethoxyethylamine (0.44 g.) in MeOH (3 ml.) was kept at room temperature for 48 hours and then evaporated to dryness. The residue was dissolved in concentrated aqueous HCl and the solution heated at 90° for 30 minutes and then evaporated to dryness. The residue was partitioned between H₂O and EtOAc and the aqueous phase basified with 10N NaOH and then extracted with EtOAc. The EtOAc extract was dried and evaporated to dryness and the residue dissolved in acetone. This solution was added to a solution of maleic acid in acetone, and the precipitate (0.12 g.) was collected and crystallised from EtOH to give 1-methyl-2-[4-(2-[2-(2,2,2-trifluoroethyl)guanidino]pyrid-6-ylthio)-butyl]imidazole hydrogen maleate, m.p. 107°–110°.

The starting material may be prepared in a similar manner to that described in Example 11, parts 2 to 5 and the first half of part 6, using 5-bromovaleronitrile in place of 4-bromobutyronitrile.

EXAMPLES 35–66

The process described in Example 5 was repeated using the appropriate starting materials and the following compounds were thus obtained:

| Example | R¹ | —Het— | —A— | R² | R³ |
|---------|-----|-------|------|-----|-----|
| 35 | CF₃CH₂ | pyridine | —S(CH₂)₃— | CH₃ | H |
| 36 | CF₃CH₂ | pyridine | —(CH₂)₄— | CH₃ | COOCH₃ |
| 37 | CF₃CH₂ | pyridine | —(CH₂)₅— | H | CH₃ |

-continued

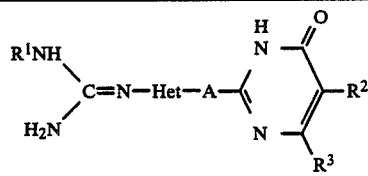

| Example | R¹ | —Het— | —A— | R² | R³ |
|---|---|---|---|---|---|
| 38 | CF₃CH₂ | pyrimidine | —(CH₂)₄— | H | CH₃ |
| 39 | CF₃CH₂ | pyrimidine | —(CH₂)₄— | CH₃ | CH₃ |
| 40 | CF₃CH₂ | pyrimidine | —(CH₂)₄— | Cl | CH₃ |
| 41 | CF₃CH₂ | pyrimidine | —(CH₂)₄— | H | H |
| 42 | CF₃CH₂ | pyrimidine | —(CH₂)₄— | C₂H₅ | H |
| 43 | CF₃CH₂ | pyrimidine | —(CH₂)₅— | H | n-C₃H₇ |
| 44 | CF₃CH₂ | pyrimidine | —(CH₂)₅— | CH₃ | H |
| 45 | CF₃CH₂ | pyrimidine | —(CH₂)₄— | CH₂-pyridyl | H |
| 46 | CF₃CH₂ | pyrimidine | —(CH₂)₄— | n-C₄H₉ | CH₃ |
| 47 | CF₃CH₂ | pyrimidine | —(CH₂)₄— | CH₂-phenyl | CH₃ |
| 48 | CF₃CH₂ | pyrimidine | —(CH₂)₄— | n-C₃H₇ | H |

-continued

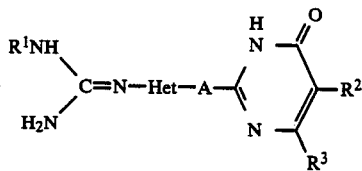

| Example | R¹ | —Het— | —A— | R² | R³ |
|---|---|---|---|---|---|
| 49 | $CHF_2CF_2CH_2$ | pyrimidine | $-(CH_2)_4-$ | H | $CH_3$ |
| 50 | $CHF_2CF_2CH_2$ | pyrimidine | $-(CH_2)_4-$ | $C_2H_5$ | H |
| 51 | $CHF_2CF_2CH_2$ | pyrimidine | $-(CH_2)_4-$ | $CH_3$ | H |
| 52 | $CF_3CH_2$ | pyrimidine | $-(CH_2)_4-$ | H | $n-C_3H_7$ |
| 53 | $CHF_2CF_2CH_2$ | pyrimidine | $-(CH_2)_4-$ | $n-C_4H_9$ | $CH_3$ |
| 54 | $CHF_2CF_2CH_2$ | pyrimidine | $-(CH_2)_4-$ | $CH_3$ | $CH_3$ |
| 55 | $CF_3CH_2$ | pyrimidine | $-(CH_2)_2O(CH_2)_2-$ | H | $CH_3$ |
| 56 | $CF_3CH_2$ | pyrimidine | $-O(CH_2)_4-$ | $CH_3$ | H |
| 57 | $CF_3CH_2$ | pyrimidine | $-O(CH_2)_3-$ | $CH_3$ | H |
| 58 | $CF_3CH_2$ | pyrimidine | $-O(CH_2)_4-$ | $C_2H_5$ | H |
| 59 | $CF_3CH_2$ | pyrimidine | $-O(CH_2)_3-$ | $C_2H_5$ | H |

-continued

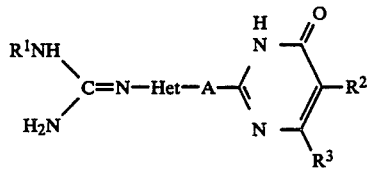

| Example | R¹ | —Het— | —A— | R² | R³ |
|---|---|---|---|---|---|
| 60 | $CHF_2CF_2CH_2$ | pyrazine | —O(CH$_2$)$_3$— | $CH_3$ | H |
| 61 | $CF_3CH_2$ | pyrazole | —(CH$_2$)$_4$— | $CH_3$ | H |
| 62 | $CF_3CH_2$ | pyrazole | —(CH$_2$)$_4$— | $CH_2$-pyridyl | H |
| 63 | $CF_3CH_2$ | pyrazole | —(CH$_2$)$_4$— | $CH_2$-pyridyl | H |
| 64 | $CHF_2CF_2CH_2$ | pyrazole | —(CH$_2$)$_4$— | $CH_3$ | H |
| 65 | $CHF_2CF_2CH_2$ | pyridine | —S(CH$_2$)$_4$— | $CH_3$ | H |
| 66 | $CF_3CH_2$ | pyridine | —S(CH$_2$)$_4$— | $CH_3$ | H |

Notes

In the above Table the group 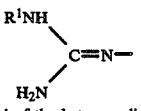

is attached to the left hand bond of the heterocyclic ring (Het) and the group A is attached to the right hand bond of the heterocyclic ring (Het). Similarly, the heterocyclic ring (Het) is attached to the left hand bond of —A— and the pyrimidone ring is attached to the right hand bond of —A—. Thus, for example, the product in Example 35 has the formula:

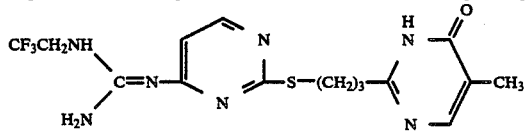

Example 35: 1H$_2$O, m.p. 210°–212° (yield 27%).
Example 36: m.p. 178°–180° (yield 18%).
Example 37: m.p. 182°–183° (yield 28%). The intermediate 6-[4-(2-[2,2,2-trifluoroethyl]guanidino)pyrimid-2-yl]hexanamidine may be prepared by a procedure similar to that described in Example 12, parts 2 to 5 inclusive, substituting ethyl 6-cyanohexanimidate for ethyl 5-cyanovalerimidate.
Example 38: m.p. 188°–190° (yield 49%).
Example 39: m.p. 211°–213° (yield 30%).
Example 40: m.p. 179°–180° (yield 6%).
Example 41: m.p. 170°–172° (yield 30%).
Example 42: m.p. 194°–196° (yield 12%).
Example 43: m.p. 164°–167° (yield 29%).
Example 44: m.p. 202°–205° (yield 52%).
Example 45: m.p. 180°–182° (yield 15%).
Example 46: m.p. 140°–142° (yield 31%).
Example 47: n.m.r. spectrum in d$_6$DMSO had the following resonances: 1.7 (m, 4H); 1.6 (m, 3H); 3.2 (s, +H$_2$O 3.8 (s, 2H); 4.1 (q, 2H); 6.4 (d, 1H); 7.2 (s, 5H); 8.1 (s, 1H); (yield 16%).
Example 48: m.p. 173°–175° (yield 26%).
Example 49: m.p. 128°–130° (yield 36%). The intermediate 5-[4-(2-[2,2,3,3-tetrafluoropropyl]guanidino)- pyrimid-2-yl]valeramidine may be prepared by a procedure similar to that described in Example 12, parts 2–5 inclusive, substituting 2,2,3,3-tetrafluoropropylisothiocyanate for 2,2,2-trifluoroethylisothiocyanate.

Example 50: maleate, m.p 170°–174° (yield 20%).
Example 51: 1.5 maleate, m.p. 162°–164° (yield 32%).
Example 52: m.p. 160°–163° (yield 43%).
Example 53: maleate, m.p. 203°–204° (yield 28%).
Example 54: maleate, m.p. 180°–182° (yield 55%).
Example 55: maleate, m.p. 145°–149° (yield 22%).
Example 56: m.p. 206°–208° (yield 57%).
Example 57: m.p. 217°–219° (yield 54%). The intermediate 4-[4-(2-[2,2,2-trifluoroethyl]guanidino)pyrimid-2-yloxy]butyramidine may be prepared by a procedure similar to that described in Example 24, parts 2 to 4, using 3-cyanopropanol instead of 4-cyanobutanol.
Example 58: maleate, m.p. 166°–168° (yield 6%).
Example 59: maleate, m.p. 205°–206° (yield 11%).
Example 60: maleate, m.p. 182°–184° (yield 25%). The 4-[4-(2-[2,2,3,3-tetrafluoropropyl]guanidino)pyrimid-2-yloxy]butyramidine used as starting material may be prepared as follows. The second, third and fourth parts of Example 34 in European Patent Publication No.30092 were repeated, using 2,2,3,3-tetrafluoropropylisothiocyanate in place of 2,2,2-trifluoroethylisothiocyanate, to give 4-[2-(2,2,3,3-tetrafluoropropyl)-guanidino]-2methylsulphinylpyrimidine. Using this intermediate, and 3-cyanopropanol in place of 4-cyanobutanol, the second, third and fourth parts of Example 24 were repeated to give the required starting material.
Example 61: n.m.r. spectrum in d$_6$DMSO had the following resonances: 7.7 (d, 1H); 7.5 (d, 1H); 5.7 (d, 1H); 4.05 (q, 2H); 3.95 (t, 2H); 1.85 (s, 3H); 1.7 (m, 4H) (yield 29%). The intermediate 5-[3-(2-[2,2,2-trifluoroethyl]guanidino)pyrazol-1-yl]valeramidine may be prepared from methyl 5-[3-(2-[2,2,2-trifluoroethyl]-guanidino)pyrazol-1-yl]valerimidate by a procedure similar to that described in Example 4, part 2, using the above imidate in place of methyl 4-[4-(2-[2,2,2-trifluoroethyl]guanidino)pyrimid-2-ylthio]butyrimidate.

Example 62: n.m.r. spectrum in d$_6$DMSO had the following resonances: 8.5 (m, 2H); 7.8 (s, 1H); 7.65 (d, 1H); 7.55 (d, 1H); 7.3 (m, 2H); 5.8 (d, 1H); 4.2 (q, 2H); 4.05 (t, 2H); 3.7 (s, 2H); 2.5 (m, 2H); 1.7 (m, 4H); (yield 36%).

Example 63: 1.25 H$_2$O, m.p. 83°–85° (yield 13%).

Example 64: maleate, m.p. 152° (yield 32%). The intermediate 5-[4-(2-[2,2,3,3-tetrafluoropropyl]-guanidino)-1,2,3-triazol-2-yl]valeramidine may be prepared by a procedure similar to that described in Example 8, parts 2 to 6 and Example 9, part 1, using 2,2,3,3-tetrafluoropropylisothiocyanate in place of 2,2,2-trifluoroethylisothiocyanate.

Example 65: maleate, m.p. 169°–170° (yield 42%). The intermediate 5-[2-(2-[2,2,3,3-tetrafluoropropyl]-guanidino)pyrid-6-ylthio]valeramidine may be prepared by a procedure similar to that described in Example 11, parts 2–6, using 5-bromovaleronitrile in place of 4-bromobutyronitrile and using 2,2,3,3-tetrafluoropropylisothiocyanate in place of 2,2,2-trifluoroethylisothiocyanate.

Example 66: maleate, m.p. 189°–191° (yield 56%). The intermediate 5-[2-(2-[2,2,2-trifluoroethyl]-guanidino)pyrid-6-ylthio]valeramidine may be prepared in a manner similar to that in Example 11, parts 2 to 6, using 5-bromovaleronitrile in place of 4-bromobutyronitrile.

EXAMPLES 67–86

The process described in Example 6 was repeated using the appropriate starting materials and the following compounds were obtained.

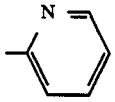

| Example | R$^1$ | —Het— | —A— | —R$^2$ |
|---|---|---|---|---|
| 67 | CF$_3$CH$_2$ | (pyrimidine) | —S(CH$_2$)$_3$— | (pyridyl) |
| 68 | CF$_3$CH$_2$ | (pyrimidine) | —S(CH$_2$)$_3$— | (phenyl) |
| 69 | CF$_3$CH$_2$ | (pyrimidine) | —S(CH$_2$)$_3$— | —CH$_3$ |
| 70 | CF$_3$CH$_2$ | (pyrimidine) | —S(CH$_2$)$_4$— | —CH$_3$ |

-continued $$\underset{H_2N}{\overset{R^1NH}{>}}C=N-Het-A-\underset{NH_2}{\overset{NNHCOR^2}{>}}$$

| Example | R¹ | —Het— | —A— | —R² |
|---|---|---|---|---|
| 71 | CHF$_2$CF$_2$CH$_2$ | 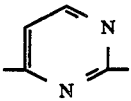 | —S(CH$_2$)$_4$— | —CH$_3$ |
| 72 | CHF$_2$CF$_2$CH$_2$ | 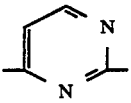 | —S(CH$_2$)$_4$— | n-C$_4$H$_9$— |
| 73 | CF$_3$CH$_2$ | 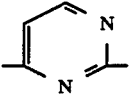 | —(CH$_2$)$_5$— | —CH$_3$ |
| 74 | CF$_3$CH$_2$ | 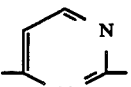 | —(CH$_2$)$_4$— | —CH$_3$ |
| 75 | CHF$_2$CF$_2$CH$_2$ | 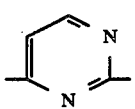 | —(CH$_2$)$_4$— | —CH$_3$ |
| 76 | CF$_3$CH$_2$ |  | —O(CH$_2$)$_3$— | —CH$_3$ |
| 77 | CF$_3$CH$_2$ |  | —O(CH$_2$)$_3$— | 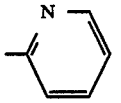 |
| 78 | CF$_3$CH$_2$ | 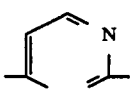 | —O(CH$_2$)$_3$— | 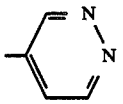 |
| 79 | CF$_3$CH$_2$ | 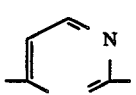 | —O(CH$_2$)$_4$— | —CH$_3$ |
| 80 | CF$_3$CH$_2$ | 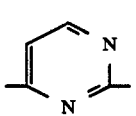 | —O(CH$_2$)$_3$— | 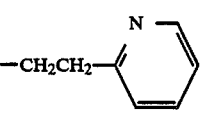 |
| 81 | CF$_3$CH$_2$ | 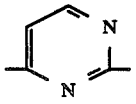 | —O(CH$_2$)$_4$— | n-C$_3$H$_7$— |
| 82 | CF$_3$CH$_2$ | 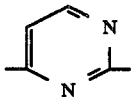 | —O(CH$_2$)$_3$— | 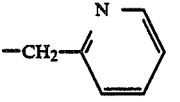 |

-continued

| | R¹NH  NNHCOR² |
| | C=N—Het—A—C |
| | H₂N  NH₂ |

| Example | R¹ | —Het— | —A— | —R² |
|---|---|---|---|---|
| 83 | CF₃CH₂ | pyridine | —S(CH₂)₃— | —CH₃ |
| 84 | CClF₂CH₂ | pyridine | —S(CH₂)₄— | —CH₃ |
| 85 | CHF₂CF₂CH₂ | pyridine | —S(CH₂)₄— | —CH₃ |
| 86 | CF₃CH₂ | pyridine | —S(CH₂)₄— | —CH₃ |

Notes

In the above Table the group 
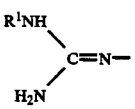
is attached to the left hand bond of the heterocyclic ring (—Het—) and the group —A— is attached to the right hand bond of the heterocyclic ring (—Het—). Similarly, the heterocyclic ring (Het) is attached to the left hand bond of —A— and the amidine is attached to the right hand bond of —A—. Thus, for example, the product in Example 67 has the formula:

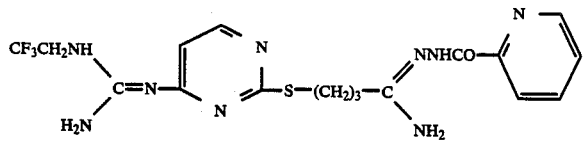

Example 67: n.m.r. spectrum in d₆DMSO had the following resonances: 1.95 (m, 2H); 2.2 (m, 2H); 3.05 (t, 2H); 4.15 (q, 2H); 6.34 (d, 3H); 7.25 (s, 1H); 7.59 (m, 1H); 7.8–8.2 (m, 5H); 8.63 (m, 1H); 10.1 (s, 1H).

Example 68: m.p. 149°–152° (yield 67%).
Example 69: m.p. 183°–185° (yield 47%).
Example 70: m.p. 156°–158° (yield 86%). The intermediate methyl 5-[4-(2-[2,2,2-trifluoroethyl]guanidino)-pyrimid-2-ylthio]valerimidate may be prepared by a process similar to that described in Example 1, parts 2 to 4 and Example 3, part 2, using 5-bromovaleronitrile in place of 4-chlorobutyronitrile.

Example 71: m.p. 153°–155° (yield 36%). The intermediate methyl 5-[4-(2-[2,2,3,3-tetrafluoropropyl]-guanidino)pyrimid-2-ylthio]valerimidate may be prepared by a procedure similar to that described in Example 1, parts 2 to 4 and Example 3, part 1, using 5-bromovaleronitrile in place of 4-chlorobutyronitrile and 2,2,3,3-tetrafluoropropylisothiocyanate in place of 2,2,2-trifluoroethylisothiocyanate.

Example 72: m.p. 170°–172° (yield 64%).
Example 73: m.p. 123°–126° (yield 52%).
Example 74: m.p. 187°–189° (yield 43%).
Example 75: m.p. 163°–164° (yield 70%).
Example 76: m.p. 149°–152° (yield 50%).
Example 77: m.p. 151°–153° (yield 19%).
Example 78: m.p. 191°–193° (yield 65%).
Example 79: m.p. 156°–158° (yield 89%).
Example 80: m.p. 82°–86° (yield 31%).
Example 81: m.p. 130°–133° (yield 55%).
Example 82: m.p. 159°–161° (yield 74%).
Example 83: m.p. 173°–175° (yield 61%).
Example 84: m.p. 132°–134° (yield 63%). The intermediate methyl 5-[2-(2-[2-chloro-2,2-difluoroethyl]-guanidino)pyrid-6-ylthio]valerimidate may be prepared by a procedure similar to that described in Example 11, parts 2 to 5 and the first half of part 6, using 5-bromovaleronitrile in place of 4-bromobutyronitrile and 2-chloro-2,2-difluoroethylisothiocyanate in place of 2,2,2-trifluoroethylisothiocyanate.

Example 85: m.p. 136°–137° (yield 82%).
Example 86: m.p. 134°–135° (yield 54%).

EXAMPLES 87–110

The process described in Example 7 was repeated using the appropriate N-acylaminoamidine as starting material, to give the following compounds:

$$\underset{H_2N}{\overset{R^1NH}{>}}C=N-Het-A-\overset{N-N}{\underset{\underset{H}{N}}{\Big\langle}}R^2$$

| Example | R¹ | —Het— | —A— | R² |
|---------|-----|-------|------|-----|
| 87 | CF₃CH₂ | pyrimidine | —S(CH₂)₃— | phenyl |
| 88 | CF₃CH₂ | pyrimidine | —S(CH₂)₃— | CH₃ |
| 89 | CF₃CH₂ | pyrimidine | —S(CH₂)₄— | CH₃ |
| 90 | CHF₂CF₂CH₂ | pyrimidine | —S(CH₂)₃— | CH₃ |
| 91 | CHF₂CF₂CH₂ | pyrimidine | —S(CH₂)₄— | n-C₄H₉ |
| 92 | CHF₂CF₂CH₂ | pyrimidine | —S(CH₂)₄— | n-C₃H₇ |
| 93 | CHF₂CF₂CH₂ | pyrimidine | —S(CH₂)₄— | CH₃ |
| 94 | CF₃CH₂ | pyrimidine | —(CH₂)₅— | CH₃ |
| 95 | CF₃CH₂ | pyrimidine | —(CH₂)₄— | CH₃ |
| 96 | CHF₂CF₂CH₂ | pyrimidine | —(CH₂)₄— | CH₃ |
| 97 | CF₃CH₂ | pyrimidine | —O(CH₂)₃— | CH₃ |
| 98 | CF₃CH₂ | pyrimidine | —O(CH₂)₄— | CH₃ |

-continued $$\underset{H_2N}{\overset{R^1NH}{>}}C=N-Het-A-\overset{N=N}{\underset{\underset{H}{N}}{\bigvee}}R^2$$

| Example | R¹ | —Het— | —A— | R² |
|---|---|---|---|---|
| 99 | CF₃CH₂ | 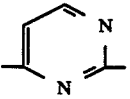 pyrimidine | —O(CH₂)₄— | n-C₃H₇ |
| 100 | CF₃CH₂ | 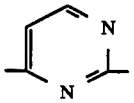 pyrimidine | —O(CH₂)₃— | 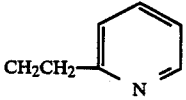 CH₂CH₂-2-pyridyl |
| 101 | CF₃CH₂ | 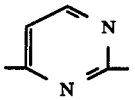 pyrimidine | —O(CH₂)₃— | n-C₃H₇ |
| 102 | CF₃CH₂ | 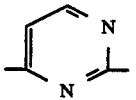 pyrimidine | —O(CH₂)₃— | 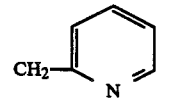 CH₂-2-pyridyl |
| 103 | CF₃CH₂ | 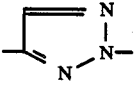 pyrazole | —(CH₂)₄— | CH₃ |
| 104 | CHF₂CF₂CH₂ | 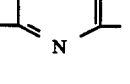 pyridine | —S(CH₂)₄— | CH₃ |
| 105 | CF₃CH₂ | 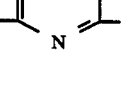 pyridine | —S(CH₂)₄— | CH₃ |
| 106 | CHF₂CF₂CH₂— | 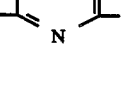 pyridine | —S(CH₂)₃— | CH₃ |
| 107 | CF₃CH₂ | 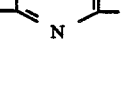 pyridine | —O(CH₂)₃— | CH₃ |
| 108 | CF₃CH₂ | 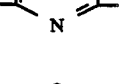 pyrimidine | —(CH₂)₂O(CH₂)₂— | CH₃ |
| 109 | CF₃CH₂ | 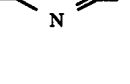 pyridine | —S(CH₂)₃— | CH₃ |

-continued

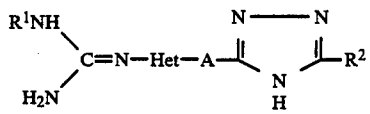

| Example | R¹ | —Het— | —A— | R² |
|---|---|---|---|---|
| 110 | CClF$_2$CH$_2$ | (pyridine) | —S(CH$_2$)$_3$— | CH$_3$ |

Notes

In the above Table the group $\underset{H_2N}{\overset{R^1NH}{>}}C=N-$ is attached to the left hand bond of the heterocyclic ring (—Het—) and the group A is attached to the right hand bond of the heterocyclic ring (—Het—). Similarly, the heterocyclic ring (—Het—) is attached to the left hand bond of —A— and the triazole ring is attached to the right hand bond of —A—. Thus, for example, the product in Example 87 has the formula:

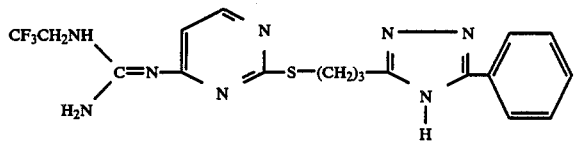

Example 87: m.p. 185°–186° (yield 80%).
Example 88: 1.5 maleate, m.p. 152°–155° (yield 48%).
Example 89: 1.75 maleate, m.p. 148°–151° (yield 26%).
Example 90: 2 maleate, m.p. 159°–161° (yield 71%).
Example 91: 2 maleate, m.p. 162°–164° (yield 58%).
Example 92: 1.5 maleate, m.p. 140°–142° (yield 35%).
Example 93: 2 maleate, m.p. 149°–152° (yield 74%).
Example 94: m.p. 189°–190° (yield 52%).
Example 95: 2 maleate, m.p. 158°–160° (yield 31%).
Example 96: 2 maleate, m.p. 137°–140° (yield 55%).
Example 97: 1.75 maleate, m.p. 163°–165° (yield 64%).
Example 98: 1.75 maleate, m.p. 147°–149° (yield 11%).
Example 99: 2 maleate, m.p. 130°–132° (yield 28%).
Example 100: 2.5 maleate, m.p. 141°–144° (yield 53%).
Example 101: 2 maleate, m.p. 141°–143° 1 (Yield 46%).
Example 102: 1.5 maleate, m.p. 152°–155° (yield 32%).
Example 103: m.p. 119°–120° (yield 33%).
Example 104: 2 maleate, m.p. 128°–130° (yield 42%).

Example 105: 1.5 fumarate, m.p. 144°–146° (yield 60%).
Example 106: 2 maleate, m.p. 154°–156° (yield 78%). The intermediate methyl 4-[2-(2-[2,2,3,3-tetrafluoropropyl]quanidino)pyrid-6-ylthio]butyrimidate may be prepared by a procedure similar to that described in Example 11, parts 4 to 5 and the first half of part 6, using 2,2,3,3-tetrafluoropropylisothiocyanate in place of 2,2,2-trifluoroethylisothiocyanate.
Example 107: 1.5 fumarate, m.p. 145°–147° (yield 48%).
Example 108: 2 maleate, m.p. 137°–139° (yield 6%).
Example 109: 2 maleate, m.p. 157°–159° (yield 75%).
Example 110: maleate, m.p. 153°–154° (yield 38%). The intermediate methyl 4-[2-(2-[2-chloro-2,2-difluoroethyl]guanidino)pyrid-6-ylthio]butyrimidate may be prepared by a procedure similar to that described in Example 11, parts 4 to 5 and the first half of part 6, using 2-chloro-2,2-difluoroethylisothiocyanate in placeof 2,2,2-trifluoroethylisothiocyanate.

EXAMPLES 111–120

The process of Example 3 was repeated using the appropriate starting materials to give the following compounds:

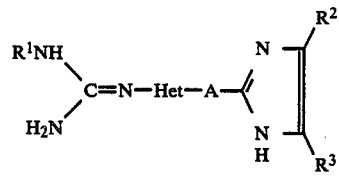

| Example | R¹ | —Het— | —A— | R² | R³ |
|---|---|---|---|---|---|
| 111 | CF$_3$CH$_2$ | (pyrimidine) | —S(CH$_2$)$_4$— | H | H |

-continued $$\begin{array}{c} R^1NH \\ \diagdown \\ C=N-Het-A \\ \diagup \\ H_2N \end{array} \begin{array}{c} N \diagup R^2 \\ \diagdown \\ N \diagdown R^3 \\ H \end{array}$$

| Example | $R^1$ | —Het— | —A— | $R^2$ | $R^3$ |
|---------|-------|-------|-----|-------|-------|
| 112 | $CF_3CH_2$ | pyrimidine | $-(CH_2)_4-$ | H | H |
| 113 | $CF_3CH_2$ | pyrimidine | $-(CH_2)_5-$ | H | H |
| 114 | $CF_3CH_2$ | pyrimidine | $-(CH_2)_4-$ | $CH_3$ | $-CH_2-$imidazole |
| 115 | $CHF_2CF_2CH_2$ | pyrimidine | $-(CH_2)_4-$ | H | H |
| 116 | $CF_3CH_2$ | pyrimidine | $-(CH_2)_2O(CH_2)_2-$ | H | H |
| 117 | $CF_3CH_2$ | pyrimidine | $-O(CH_2)_3-$ | H | H |
| 118 | $CHF_2CF_2CH_2$ | pyrazole | $(CH_2)_4$ | H | H |
| 119 | $CHF_2CF_2CH_2$ | pyridine | $-S(CH_2)_3-$ | H | H |
| 120 | $CF_3CH_2$ | pyrimidine | $-(CH_2)_4-$ | $CH_3$ | $CH_3$ |

Notes

In the above Table the group $\begin{array}{c} R^1NH \\ \diagdown \\ C=N- \\ \diagup \\ H_2N \end{array}$ is attached to the left hand bond of the heterocyclic ring (—Het—) and the group —A— is attached to the right hand bond of the heterocyclic ring (—Het—). Similarly, the left hand bond of —A— is attached to the heterocyclic ring and the right hand bond of —A— is attached to the imidazole ring. Thus, for example, the product in Example 111 has the formula:

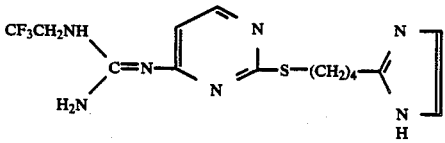

Example 111: 2 maleate, m.p. 165°–167° (yield 11%).
Example 112: 1.3 oxalate, m.p. 254° (yield 10%).
Example 113: m.p. 193°–195° (yield 30%).
Example 114: m.p. 197°–200° (yield 40%).
Example 115: 2 maleate, m.p. 155°–158° (yield 40%).
Example 116: m.p. 135°–137° (yield 13%).
Example 117: 2 maleate, m.p. 173°–175° (yield 17%).
Example 118: 2 maleate, m.p. 135°–137° (yield 18%).
Example 119: 2 maleate, m.p. 170°–172° (yield 37%).
Example 120: 2 maleate, m.p. 166°–168° (yield 11%).

EXAMPLES 121–122

The process described in Example 25 was repeated using 2-(2-hydroxyethylthio)imidazole and 2-(3-hydroxypropylthio)imidazole in place of 3-methyl-5-(3-hydroxypropylthio)-1,2,4-triazole to give 2-(2-[4-(2-[2,2,2-trifluoroethyl]guanidino)pyrimid-2-yloxy]ethylthio)imidazole dimaleate, m.p. 119°–121° (yield 28%) and 2-(3-[4-(2-[2,2,2-trifluoroethyl]guanidino)pyrimid-2-yloxy]propylthio)imidazole 1.5 fumarate, m.p. 122°–124° (yield 31%) respectively.

The substituted imidazoles used as starting materials may be prepared by reaction of 2-mercaptoimidazole with 2-bromoethanol and 3-chloropropanol according to the method described in the second part of Example 25.

EXAMPLE 123

The process of Example 34 was repeated using the appropriate iminoether as starting material to give 1-methyl-2-[2-(2-[2,2,2-trifluoroethyl]guanidino)pyrid-6-yloxy]propyl)imidazole, 2 maleate, m.p. 142°–144° (yield 34%).

EXAMPLE 124

The process of Example 21 was repeated using the appropriate amidine as starting material to give 4-amino-2-(4-[4-(2-[2,2,2-trifluoroethyl]guanidino)pyrimid-2yl]butyl)pyrimidine. 2.25 maleate, m.p. 180°–182° (yield 27%).

EXAMPLE 125

4-Amino-2-methylsulphinylpyrimidine (0.16 g.) was added to a stirred mixture of 4-[2-(2,2,2-trifluoroethyl)-guanidino-2-(3-hydroxypropoxy)pyrimidine (0.15 g.), t-butanol (5 ml.) and a 50% w/w dispersion of sodium hydride in oil (0.05 g.) at 50° and the resulting mixture stired at 50° for 6 hours. The mixture was evaporated to dryness and the residue partitioned between HCl and ether. The aqueous phase was basified with 1N NaOH and then extracted with EtOAc and the EtOAc extract was dried and evaporated to dryness. A solution of the residue in acetone was added to a solution of maleic acid in acetone and the precipitate was collected and crystallised from EtOH to give 4-amino-2-[3-(4-[2-(2,2,2-trifluoroethyl)guanidino]pyrimid-2-yloxy)-propyloxy]pyrimidine bis hydrogen maleate (0.13 g.), m.p. 136°–137°.

The starting materials may be prepared as follows:
Sodium metaperiodate (1.3 g.) in water (5 ml.) was added to a solution of 4-amino-2-methylthiopyrimidine (0.7 g.) in water (10 ml.) at 90°, and the solution kept at 90° for 1 hour. A further 1.3 g. of sodium metaperiodate was added and the solution heated a further 0.5 hours and then cooled to room temperature. The mixture was filtered and the filtrate evaporated to dryness. The residue was triturated with MeOH and the suspension filtered and then the filtrate was evaporated to dryness. The residue was triturated with acetonitrile and the insoluble solid collected to give 4-amino-2-methylsulphinylpyrimidine (0.7 g.) which was used without further purification.

A suspension of 4-[2-(2,2,2-trifluoroethyl)guanidino]-2-methylthiopyrimidine (European Patent Publication No.30092; 5.3 g.) in chloroform (500 ml.) was treated with 3-chloroperbenzoic acid (12 g., 85% w/w) and the solution left at room temperature for 18 hours. The mixture was washed twice with a solution of a mixture of potassium carbonate (10 g.) and sodium sulphite (2 g.) in water (50 ml.), and then dried and evaporated to dryness. The residue was fractionated by medium pressure liquid chromatography on Merck "Kieselgel 60" to give 4-[2-(2,2,2-trifluoroethyl)guanidino]-2-methylsulphonylpyrimidine (2.2 g.), m.p. 158°–159° (after recrystallisation from EtOH).

A 50% w/w dispersion of sodium hydride in oil (0.048 g.) was added to propane-1,3-diol (0.5 ml.) and the mixture stirred at room temperature for 0.5 hours. 4-[2-(2,2,2-Trifluoroethyl)guanidino]-2-methanesulphonylpyrimidine (0.15 g.) was added and the mixture heated at 90° with occasional shaking for 0.5 hours and then cooled to room temperature. The mixture was taken up in N aqueous HCl and washed with EtOAc. The aqueous phase was basified with 10N aqueous NaOH and then extracted three times with EtOAc. The combined extracts were dried and evaporated to dryness. A solution of the residue in acetone was added to a solution of maleic acid in acetone, and the precipitate collected to give 4-[2-(2,2,2-triflurooethyl)guanidino]-2-(3-hydroxypropoxy)pyrimidine hydrogen maleate (0.19 g.), m.p. 165°–166° (after reacrystallisation from EtOH).

EXAMPLE 126

The process of Example 18 and 22 was repeated using the appropriate iminoether as starting material to give 5-hydroxy-3-(4-[4-(2-[2,2,2-trifluoroethyl]guanidino)-pyrimid-2-yloxy]butyl)-1,2,4-triazole maleate, m.p. 206°–208° (yield 12%).

EXAMPLE 127–141

The process of Example 13 was repeated using the appropriate iminoether as starting material and the following compounds were obtained:

$$R^1NH\diagdown C=N-Het-A-C \diagup NCN$$
$$H_2N \diagup \phantom{C=N-Het-A-C} \diagdown NH_2$$

| Example | $R^1$ | —Het— | —A— |
|---|---|---|---|
| 127 | $CF_3CH_2$ | pyridine (N,N) | $-S(CH_2)_4-$ |
| 128 | $CHF_2CF_2CH_2$ | pyridine (N,N) | $-S(CH_2)_3-$ |
| 129 | $CHF_2CF_2CH_2$ | pyridine (N,N) | $-S(CH_2)_4-$ |

-continued $$\begin{array}{c} R^1NH \\ \phantom{R^1}C=N-Het-A-C \\ H_2N \end{array} \begin{array}{c} NCN \\ \phantom{NCN} \\ NH_2 \end{array}$$

| Example | R¹ | —Het— | —A— |
|---|---|---|---|
| 130 | CF₃CH₂ | (4-methyl-pyrimidin-2,?-diyl) | —(CH₂)₂O(CH₂)₂— |
| 131 | CF₃CH₂ | (4-methyl-pyrimidin-2,?-diyl) | —(CH₂)₄— |
| 132 | CF₃CH₂ | (4-methyl-pyrimidin-2,?-diyl) | —(CH₂)₅— |
| 133 | CF₃CH₂ | (4-methyl-pyrimidin-2,?-diyl) | —O(CH₂)₄— |
| 134 | CF₃CH₂ | (4-methyl-pyrimidin-2,?-diyl) | —O(CH₂)₃— |
| 135 | CF₃CH₂ | (pyrazole-diyl) | —(CH₂)₄— |
| 136 | CF₃CH₂ | (pyrazole-diyl) | —(CH₂)₄— |
| 137 | CF₃CH₂ | (triazole-diyl) | —(CH₂)₄— |
| 138 | CF₃CH₂ | (2,6-dimethylpyridin-diyl) | —S(CH₂)₃— |
| 139 | CClF₂CH₂ | (2,6-dimethylpyridin-diyl) | —S(CH₂)₄— |
| 140 | CHF₂CF₂CH₂ | (2,6-dimethylpyridin-diyl) | —S(CH₂)₄— |

-continued $$\begin{array}{c} R^1NH \\ \phantom{R^1}C=N-Het-A-C \\ H_2N \end{array} \begin{array}{c} NCN \\ \phantom{NCN} \\ NH_2 \end{array}$$

| Example | R¹ | —Het— | —A— |
|---|---|---|---|
| 141 | CF₃CH₂ | (2,6-dimethylpyridin-diyl) | —S(CH₂)₄— |

Notes

In the above Table the group $$\begin{array}{c} R^1NH \\ \phantom{R^1}C=N- \\ H_2N \end{array}$$

is attached to the left hand bond of the heterocyclic ring (—Het—) and the group —A— is attached to the right hand bond of the heterocyclic group (—Het—). Similarly, the left hand bond of —A— is attached to the heterocyclic ring (—Het—) and the right hand bond of —A— is attached to the N—cyanoamidine. Thus, for example, the product in Example 127 has the formula:-

$$\begin{array}{c} CF_3CH_2NH \\ \phantom{CF_3CH_2}C=N \\ H_2N \end{array} \begin{array}{c} \\ \end{array} \begin{array}{c} N \\ \phantom{N}C-S-(CH_2)_4-C \\ N \end{array} \begin{array}{c} NCN \\ \phantom{NCN} \\ NH_2 \end{array}$$

Example 127: maleate 1H₂O, m.p. 148° (yield 28%).
Example 128: m.p. 197°–198° (yield 16%).
Example 129: 1.25 maleate, m.p. 168°–169° (yield 40%).
Example 130: m.p. 175°–177° (yield 48%).
Example 131: m.p. 162°–164° (yield 30%).
Example 132: m.p. 180°–183° (yield 37%).
Example 133: m.p. 168°–170° (yield 70%).
Example 134: m.p. 172°–174° (yield 73%).
Example 135: 1 maleate. 0.5H₂O, m.p. 129°–130°.
Example 136: m.p. 181°–183° (yield 53%).
Example 137: maleate, m.p. 142°–144° (yield 33%).
Example 138: maleate, m.p. 129°–130° (yield 61%).
Example 139: maleate, m.p. 125°–127° (yield 73%).
Example 140: maleate, m.p. 123°–125° (yield 54%).
Example 141: maleate, m.p. 118°–119° (yield 63%).

EXAMPLES 142–146

The process of Example 33 was repeated using the appropriate iminoether as starting material and the following compounds were obtained:

$$\begin{array}{c} R^1NH \\ \phantom{R^1}C=N-Het-A-C \\ H_2N \end{array} \begin{array}{c} NSO_2NH_2 \\ \phantom{NSO_2NH_2} \\ NH_2 \end{array}$$

| Example | R | —Het— | —A— |
|---|---|---|---|
| 142 | CF₃CH₂ | (4-methyl-pyrimidin-2,?-diyl) | —S(CH₂)₃— |
| 143 | CF₃CH₂ | (4-methyl-pyrimidin-2,?-diyl) | —(CH₂)₄— |

-continued

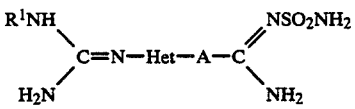

| Example | R | —Het— | —A— |
|---|---|---|---|
| 144 | CF$_3$CH$_2$ | (4-methyl-pyrimidin-2-yl) | —(CH$_2$)$_5$— |
| 145 | CF$_3$CH$_2$ | (4-methyl-pyrimidin-2-yl) | —O(CH$_2$)$_4$— |
| 146 | CHF$_2$CF$_2$CH$_2$ | (6-methyl-pyridin-2-yl) | —S(CH$_2$)$_3$— |

Notes

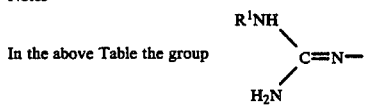

In the above Table the group is attached to the left hand bond of the heterocyclic ring (—Het—) and the group —A— is attached to the right hand bond of the heterocyclic group (—Het—). Similarly the left hand bond of —A— is attached to the heterocyclic ring (—Het—) and the right hand bond of —A— is attached to the sulphamoylamidine radical. Thus, for example, the product in Example 142 has the formula:-

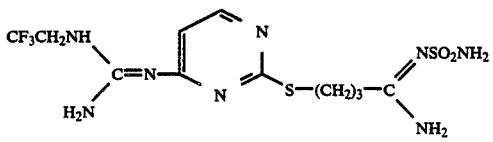

Example 142: 1.25 maleate, 1H$_2$O, m.p. 124°–27° (yield 15%).
Example 143: maleate, m.p. 178°–180° (yield 11%).
Example 144: 1.5 maleate, m.p. 149°–152° (yield 13%).
Example 145: m.p. 193°–195° (yield 3.5%).
Example 146: maleate, m.p. 118°–120° (yield 19%).

EXAMPLES 147–152

The process of Example 17 was repeated using the appropriate iminoether as starting material and the following compounds were thus obtained:

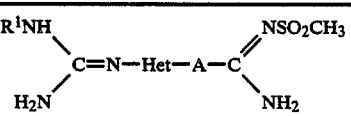

| Example | R | —Het— | —A— |
|---|---|---|---|
| 147 | CF$_3$CH$_2$ | (4-methyl-pyrimidin-2-yl) | —(CH$_2$)$_5$— |
| 148 | CHF$_2$CF$_2$CH$_2$ | (4-methyl-pyrimidin-2-yl) | —(CH$_2$)$_4$— |
| 149 | CF$_3$CH$_2$ | (4-methyl-pyrimidin-2-yl) | —(CH$_2$)$_2$O(CH$_2$)$_2$— |
| 150 | CF$_3$CH$_2$ | (4-methyl-pyrimidin-2-yl) | —O(CH$_2$)$_4$— |
| 151 | CF$_3$CH$_2$ | (6-methyl-pyridin-2-yl) | —S(CH$_2$)$_3$— |
| 152 | CClF$_2$CH$_2$ | (6-methyl-pyridin-2-yl) | —S(CH$_2$)$_3$— |

Notes

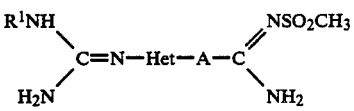

In the above Table the group is attached to the left hand bond of the heterocyclic group (—Het—) and the group —A— is attached to the right hand bond of the heterocyclic group (—Het—). Similarly the left hand bond of —A— is attached to the heterocyclic ring (—Het—) and the right hand bond of —A— is attached to the methylsulphonylamidine radical. Thus, for example, the product in Example 150 has the formula:-

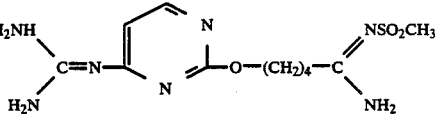

Example 147: maleate, n.m.r. spectrum in d$_6$DMSO had the following resonances: 1.5 (m, 6H); 2.1 (t, 2H); 2.8 (t, 2H); 4.3 (q, 2H); 6.1 (s, 2H); 6.8 (d, 1H); 8.4 (d, 1H).
Example 148: maleate, m.p. 142°–146° (yield 18%).
Example 149: maleate, m.p. 109°–112° (yield 21%).
Example 150: maleate, m.p. 169°–170° (yield 7%).
Example 151: maleate, m.p. 131°–132° (yield 40%).
Example 152: maleate, m.p. 145°–147° (yield 50%).

EXAMPLE 153

The process of Example 19 was repeated using the appropriate iminoether as starting material to give N-(4-methylimidazol-2-yl)-3-(2-[4-(2-[2,2,2-trifluoroethyl]-guanidino)pyrimid-2-yl]ethoxy)propionamidine. 3 maleate, m.p. 138°–141° (yield 8%).

EXAMPLE 154

The process of Example 18 was repeated using the appropriate iminoether as starting material to give N-ethoxycarbonyl-5-[4-(2-[2,2,2-trifluoroethyl]-guanidino)pyrimid-2-yloxy]valeramidrazone, m.p. 117°–119° (yield 69%).

EXAMPLE 155

A tablet containing 50 mg. of 3-methyl-5-(4-[3-(2-[2,2,2-trifluoroethyl]guanidino)pyrazol-1-yl]butyl)-1,2,4-triazole may be prepared using ingredients in the following proportions:

|  | mg./tablet |
|---|---|
| (a) Tablet Core |  |
| Active agent | 50 |
| Lactose | 218.5 |
| Calcium carboxymethylcellulose | 22.5 |
| Polyvinylpyrrolidone | 6.0 |
| Magnesium stearate | 3.0 |
| (b) Tablet Coat |  |
| Hydroxypropylmethylcellulose | 4.5 |
| Polyethylene glycol | 0.9 |
| Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

We claim:

1. A guanidine derivative of the formula I:

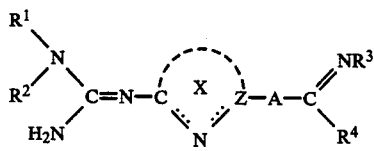

in which
- $R^1$ and $R^2$, which may be the same or different, are hydrogens or branched or unbranched 1-10C alkyls, 3-8C cycloalkyls or 4-14C cycloalkylalkyls, each alkyl, cycloalkyl or cycloalkylalkyl being optionally substituted by one or more halogens selected from fluorine, chlorine and bromine, provided that at least one of $R^1$ and $R^2$ is a halogen-substituted alkyl, cycloalkyl or cycloalkylakyl and provided that there is no halogen on the carbon of the alkyl, cycloalkyl or cycloalkylalkyl which is directly attached to the nitrogen atom;
- in ring X the dotted line is a double bond on one side of the nitrogen and Z is a carbon or nitrogen such that ring X is a 5-membered aromatic heterocyclic ring selected from the group consisting of oxazole, thiazole, imidazole, 1,2,4-thiadiazole, 1,2,4-oxadiazole, 1,2,3-triazole, 1,2,4-triazole and pyrazole, which heterocyclic ring may, where possible, carry one or two optional substituents, the optional substituents on ring X being selected from fluorine, chlorine, bromine, 1-6C alkyl, 1-6C alkoxy, trifluoromethyl, hydroxy and amino;
- —A— is phenylene or 5-7C cycloalkylene or a 1-8C alkylene chain which is optionally substituted by one or two 1-3C alkyls and into which is optionally inserted, as part of the backbone of the chain, one or two groups selected from oxygen, sulphur, NH, 1-6C N-alkyl, cis and trans vinylene, ethynylene, phenylene and 5-7C cycloalkylene, provided that the shortest link between ring X and $C(R^4)=NR^3$ is of at least 3 atoms, provided that when an optional insertion is made in chain A which results in the inserted group being directly attached to $C(R^4)=NR^3$ the inserted group is other than NH or N-alkyl, and provided that no two insertions selected from oxygen, sulphur, NH and N-alkyl are directly attached one to the other;
- $R^4$ is of the formula $NHR^7$ and $R^3$ and $R^7$ are joined to form, together with the N—C=N chain to which they are attached, a monocyclic heterocyclic ring system composed of a 5-membered ring selected from the group consisting imidazole, imidazoline, triazole, oxadiazole and thiadiazole, which ring may, where possible, carry one or two or three optional substituents selected from fluorine, chlorine, bromine, 1-6C alkyl, 1-6C alkoxyl, 1-6C alkylthio, trifluoromethyl, hydroxy, amino, phenyl, 7-11C phenylalkyl, carboxy, 2-6C carboxyalkyl, 2-6C alkoxycarbonyl, 3-10C alkoxycarbonylalkyl, 1-6C hydroxyalkyl, furyl, thienyl, pyrrolyl, thiazolyl, oxazolyl, imidazolyl, thiadiazolyl, oxadiazolyl, triazolyl, pyrazolyl and heteroaryl(1-6C)alkyl in which the heteroaryl group is selected from the group consisting of furyl, thienyl, pyrrolyl, thiazolyl, oxazolyl, imidazolyl, thiadiazolyl, oxadiazolyl, triazolyl and pyrazolyl and in which the heteroaryl may be optionally substituted by one or two substituents selected from methyl and amino;

and the pharmaceutically-acceptable acid-addition salts thereof.

2. A guanidine derivative of the formula I given in claim 1 in which $R^1$ and $R^2$ are selected from the group consisting of hydrogen, 2,2,2-trifluoroethyl, 2,2,2-trichloroethyl, 2-chloro-2,2-difluoroethyl, 2,2,-dichlorofluoroethyl, 2-bromo-2,2difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tretetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutly)methyl, ethyl, propyl, isopropyl, butyl, cyclopropyl, cyclobutly, cyclopropylmethyl and cyclopropylbutyl, provided that at least one of $R^1$ and $R^2$ is halogen-substituted, ring X is optionally substituted, where possible, by one or two substituents selected from fluorine, chlorine, bromine, methyl, methoxy, trifluoromethyl, hydroxy and amino;

—A— is phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxypropyleneoxy, oxyethyleneoxymethylene, oxyethylenethio, oxypropylenethio, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene;

the optional substituents on the ring formed by $R^3$ and $R^7$ being joined are selected from fluorine, chlorine, bromine, methyl, ethyl, n-propyl, n-butyl, methoxy, methylthio, trifluoromethyl, hydroxy, amino, phenyl, benzyl, carboxymethyl, methoxycarbonyl, methoxycarbonylmethyl, hydroxymethyl, heteroarylmethyl, 2-heteroarylethyl, furyl, thienyl, pyrrolyl, thiazolyl, oxazolyl, imidazolyl, thiadiazolyl, oxadiazolyl, triazolyl, and pyrazolyl;

and when the optional substituent is heteroarylmethyl or 2-heteroarylethyl, that heteroaryl is furyl, thienyl, pyrrolyl, thiazolyl, oxazolyl, imidazolyl, thiadiazolyl, oxadiazolyl, triazolyl, or pyrazolyl, such radical being optionally substituted by one or two substituents selected from methyl and amino:

and the pharmaceutically-acceptable acid-addition salts thereof.

3. A guanidine derivative as claimed in claim 1 or 2 in which $R^3$ and $R^7$ are joined to form an unsubstituted imidazole, or a triazole substituted in the 5-position by 1-6C alkyl.

4. A guanidine derivative as claimed in claim 3 in which $R^2$ is a hydrogen atom and $R^1$ is a 2,2,2-trifluoroethyl or 2,2,3,3-tetrafluoropropyl radical.

5. A guanidine derivative as claimed in claim 4 in which ring x is a pyrazole or 1,2,3-triazole, each of which carries no optional substituent.

6. A guanidine derivative as claimed in claim 5 in which —A— is a tetramethylene, pentamethylene, oxytrimethylene, oxytetramethylene, thiotrimethylene or thiotetramethylene radical.

7. A guanidine derivative according to claim 1 selected from the group consisting of 3-methyl-5-(4-[3-(2-[2,2,2-trifluoroethyl]guanidino)pyrazol-1-yl]butyl-1,2,4-triazole and the pharmaceutically-acceptable acid-addition salts thereof.

8. A guanidine derivative selected from the group consisting of 3-methyl-5-(4-[3-(2-[2,2,2-trifluoroethyl]-guanidino)pyrazol-1-yl]butyl-1,2,4-triazole, 2-(4-[4-(2-[2,2,2-trifluoroethyl]guanidino)-1,2,3-triazole-2-yl]butyl)imidazole, 5-methyl-3-(4-[4-(2-[2,2,2-tetrafluoropropyl]guanidino)-1,2,3-triazol-2-yl]butyl)-1,2,4-triazole, and the pharmaceutically-acceptable acid-addition salts thereof.

9. A pharmaceutical composition which comprises a guanidine derivative as claimed in claim 1 in an amount effective to inhibit gastric acid secretion in a warm-blooded animal and in association with a pharmaceutically-acceptable diluent or carrier.

10. A method of inhibiting gastric acid secretion in a warm-blooded animal which comprises administering to the animal an effective amount of a compound of claim 1.

* * * * *